US012697050B2

(12) United States Patent
Mäntele et al.

(10) Patent No.: US 12,697,050 B2
(45) Date of Patent: Aug. 4, 2026

(54) APPARATUS AND METHOD FOR ANALYTE MEASUREMENT WITH IMPROVED COUPLING OF EXCITATION RADIATION INTO MATERIAL INCLUDING SAID ANALYTE

(71) Applicant: DiaMonTech AG, Berlin (DE)

(72) Inventors: Werner Mäntele, Kiefersfelden-Mühlbach (DE); Thorsten Lubinski, Berlin (DE); Sergius Janik, Berlin (DE); Michael Kaluza, Berlin (DE)

(73) Assignee: DiaMonTech AG, Berlin (DE)

( * ) Notice: Subject to any disclaimer, the term of this patent is extended or adjusted under 35 U.S.C. 154(b) by 837 days.

(21) Appl. No.: 17/926,096

(22) PCT Filed: May 26, 2021

(86) PCT No.: PCT/EP2021/064080
§ 371 (c)(1),
(2) Date: Nov. 17, 2022

(87) PCT Pub. No.: WO2021/239828
PCT Pub. Date: Dec. 2, 2021

(65) Prior Publication Data
US 2023/0190146 A1 Jun. 22, 2023

(30) Foreign Application Priority Data

May 27, 2020 (WO) ................. PCT/EP2020/064730
Jul. 31, 2020 (WO) ................. PCT/EP2020/071711

(51) Int. Cl.
A61B 5/1455 (2006.01)
A61B 5/00 (2006.01)
A61B 5/145 (2006.01)

(52) U.S. Cl.
CPC ........ *A61B 5/14532* (2013.01); *A61B 5/1451* (2013.01); *A61B 5/1455* (2013.01);
(Continued)

(58) Field of Classification Search
CPC ... A61B 5/0075; A61B 5/1451; A61B 5/1455; A61B 5/14551; A61B 5/14552;
(Continued)

(56) References Cited

U.S. PATENT DOCUMENTS 10,258,265 B1 4/2019 Poeze et al.
10,512,407 B2 12/2019 Richards et al.
(Continued)

FOREIGN PATENT DOCUMENTS

CN 1578905 A 2/2005
CN 108369183 A 8/2018
(Continued)

OTHER PUBLICATIONS

Pleitez et al., "Photothermal deflectometry enhanced by total internal reflection enables non-invasive glucose monitoring in human epidermis," The Analyst, vol. 140, No. 2, Nov. 7, 2014, pp. 483-488, XP055211729, ISSN: 0003-2654, DOI: 10.1039/C4AN01185F.
(Continued)

*Primary Examiner* — Chu Chuan Liu
(74) *Attorney, Agent, or Firm* — Barclay Damon LLP

(57) ABSTRACT

An apparatus (10) for analyzing a material (12) comprising at least one analyte, said apparatus comprising a measurement body (16) having a contact surface (14) suitable to be brought in thermal contact or pressure-transmitting contact with said material (12), an excitation radiation source (26) configured for irradiating excitation radiation (18) into the material (12) to be absorbed therein, and a detection device for detecting a physical response of the measurement body to heat or a pressure wave received from said material (12)

(Continued)

upon absorption of said excitation radiation (18) and for generating a response signal indicative of the degree of absorption of excitation radiation, wherein a protrusion (80) is provided, said protrusion having a front surface (82) facing said material (12) and being in contact with the material when the material is brought in contact with the contact surface, and wherein said excitation radiation (18) is irradiated into the material (12) through said front surface (82) of said protrusion (80), wherein said protrusion (80) is formed on said contact surface (14) of said measurement body (16), or wherein said measurement body (16) forms said protrusion or a part of said protrusion, in which said contact surface (14) of said measurement body (16) forms at least a part of said front surface of said protrusion and is elevated with respect to a surrounding structure.

38 Claims, 17 Drawing Sheets

(52) U.S. Cl.
CPC .......... *A61B 5/6831* (2013.01); *A61B 5/6843* (2013.01); *A61B 2560/0223* (2013.01)

(58) Field of Classification Search
CPC . A61B 5/14532; A61B 5/6826; A61B 5/6843; A61B 2562/0233; A61B 2562/04
See application file for complete search history.

(56) References Cited

U.S. PATENT DOCUMENTS

| 11,832,942 | B2 * | 12/2023 | Shinohara | ............ A61B 5/1455 |
| 2004/0242978 | A1 | 12/2004 | Uchida et al. | |
| 2007/0123759 | A1 | 5/2007 | Grata et al. | |
| 2016/0058310 | A1 | 3/2016 | Iijima | |
| 2017/0146455 | A1 * | 5/2017 | Mäntele | .............. A61B 5/1455 |
| 2018/0328835 | A1 * | 11/2018 | Bauer | .................. A61B 5/1455 |
| 2018/0335381 | A1 | 11/2018 | Bauer et al. | |
| 2019/0104973 | A1 | 4/2019 | Poeze et al. | |

FOREIGN PATENT DOCUMENTS

| EP | 1254631 | A1 | 11/2002 |
| EP | 3623795 | A2 | 3/2020 |
| GB | 2357844 | A | 7/2001 |
| WO | 2017/097824 | A1 | 6/2017 |
| WO | 2020/094233 | A1 | 5/2020 |
| WO | 2020/094265 | A1 | 5/2020 |

OTHER PUBLICATIONS

International Searching Authority/EP, International Search Report and Written Opinion of the International Searching Authority, Application No. PCT/EP2021/064080, dated Nov. 16, 2021, 27 pages.
Pleitez et al., "In Vivo Noninvasive Monitoring of Glucose Concentration in Human Epidermis by Mid-Infrared Pulsed Photoacoustic Spectroscopy," Analytical Chemistry, vol. 85, No. 2, Dec. 26, 2012, pp. 1013-1020, XP055499217, ISSN: 0003-2700, DOI: 10.2021/ac302841f.

* cited by examiner

APPARATUS AND METHOD FOR ANALYTE MEASUREMENT WITH IMPROVED COUPLING OF EXCITATION RADIATION INTO MATERIAL INCLUDING SAID ANALYTE

CROSS-REFERENCE TO RELATED APPLICATIONS

This application is the national phase entry of International Patent Application No. PCT/EP2021/064080 filed on May 26, 2021, and claims the benefit of International Patent Application No. PCT/EP2020/064730 filed May 27, 2020, and International Patent Application No. PCT/EP2020/071711 filed Jul. 31, 2020, the disclosures of which are incorporated herein by reference in their entirety.

FIELD OF THE INVENTION

The present invention relates generally to apparatus and methods for analyzing a material as, for example, a fluid, comprising at least one analyte. In particular, the present invention relates to apparatus and methods for non-invasive measurement of analytes in body fluids, such as glucose concentrations in human skin, in particular in the interstitial fluid of human skin.

BACKGROUND OF THE INVENTION

The present invention relates to apparatus and methods of analyzing a material comprising at least one analyte. The apparatus comprises a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body.

The apparatus further comprises an excitation radiation source configured for irradiating excitation radiation into the material to be absorbed therein, and a detection device for detecting a physical response of the measurement body, or of a component included therein, to heat or a pressure wave received from said material upon absorption of said excitation radiation, and for generating a response signal based on said detected physical response. Herein, the response signal is indicative of the degree of absorption of excitation radiation.

The present invention is not limited to any specific physical response to heat or pressure waves received from said material upon absorption of the excitation radiation, nor to any specific way of detecting this physical response in a manner that allows for generating a response signal that is indicative of the degree of absorption of excitation radiation. Various physical responses and corresponding detection methods have been previously proposed for these types of analyte measurement procedures by the present applicant and are briefly summarized below, and each of them may be applied in the present invention.

For example, the detection device may comprise a light source for generating a detection light beam travelling through at least a portion of said measurement body or a component included in said measurement body, and said physical response of the measurement body to heat or pressure waves received from said material upon absorption of said excitation radiation may be a local change in the refractive index of said measurement body or said component. In this case, the detection device may be configured for detecting one of a change in the light path or a change in the phase of detection light beam due to said change in refractive index of the material of the measurement body or the component included in the same.

For example, in various methods and devices described in detail in two earlier applications of the present applicant, published as WO 2015/193310 A1 and WO 2017/097824 A1, both of which are included herein by reference, the measurement body is transparent for said detection light beam, and the detection light beam is directed to be totally or partially reflected at a surface of said measurement body that is in thermal contact with said material. In this case, the detection device may comprise a photodetector, in particular a position sensitive photodetector which is capable of detecting a degree of deflection, in particular a deflection angle of said detection light beam due to said local change in refractive index. Accordingly, in this case, the physical response to the heat or pressure waves received by the measurement body is a local change in refractive index, and the response signal is the detected degree of deflection which is indeed found to be indicative of the degree of absorption of the excitation radiation.

In alternative variants suggested by the present applicant, as for example disclosed in international application PCT/EP2019/064356, included herein by reference, said detection device may comprise an interferometric device allowing for assessing said change in phase of the detection beam and generating a response signal indicative of said change in phase. In this case, the physical response of the measurement body (or a component included therein) to heat or pressure waves received from said material upon absorption of said excitation radiation is again a local change in index of refraction, while the response signal is in this case an interferometric signal reflecting a change in the phase of the detection beam due to the local change in refractive index.

In yet alternative embodiments, the measurement body or a component in said measurement body may have electrical properties that change in response to a local change in temperature or a change in pressure associated therewith, and said detection device comprises electrodes for capturing electrical signals representing said electrical properties. Various possible setups are disclosed in WO 2019/110597 A2, included herein by reference. For example, the measurement body may comprise sections having piezoelectric properties, and pressure changes associated with received heat lead to electrical signals that can be recorded with the electrodes. In this case, the change in pressure resembles the physical response of the measurement body or of a component included therein, to heat received from the material upon absorption of the excitation radiation, which is detected using the piezoelectric properties of the measurement body and the electrode, and which leads to electrical signals representing the aforementioned response signal that is indicative of the degree of absorption of excitation radiation. In yet further variants, a temperature change due to received heat can be directly measured using very sensitive temperature sensors.

Note that in the following description, the physical response of the measurement body to heat received from the material is described in detail. However, it is to be understood that in various embodiments of the method and apparatus of the invention, the material is in pressure transmitting contact with the measurement body, and the physical response of the measurement body is a response to pressure waves received from the material. Herein, the expression "pressure transmitting contact" shall include all relations that allow the transfer of pressure waves from the material to the measurement body, and in particular, an acoustically coupled relation, where the coupling could be established by a gas, a liquid or a solid body. All detailed explanations given in connection with the thermal contact and physical response to heat received by the measurement body from the material shall be understood in combination with scenarios including pressure transmitting contact and physical response to pressure waves, where applicable, without explicit mention.

The apparatus may further be configured for conducting an analyzing step, in which said analyzing is carried out based, at least in part, on said response signal. For this purpose, the apparatus may comprise a control system comprising one or more processors which are programmed to carry out the analysis. If one is for example interested in determining the concentration of the analyte in the material, the excitation radiation may be chosen to have wavelengths that are characteristic for the absorption spectrum of the analyte, for example associated with absorption peaks thereof. Since the response signal is indicative of the degree of absorption of excitation radiation, in this case the response signal is directly related to the concentration of the analyte in the material. Accordingly, the analyzing step may be based at least in part on a measure of the concentration of the analyte in the material, and in some non-limiting applications, it may actually amount to determining this concentration.

For example, apparatus of the type summarized above have been employed by the applicant for non-invasive measuring of a glucose level of a user. In this specific application, the "analyte" is formed by glucose, and the "material" is the skin of the user. It has been previously demonstrated that this approach allows for very precise measurement of glucose concentration in the interstitial fluid within the skin of a person, which is found to be directly related with and hence representative of the glucose content of the patient's blood. Shown in FIG. 4 of the present application is the result of a Clark's error grid analysis taken from WO 2017/097824 A1, demonstrating that the above apparatus and analysis method allow for predicting the actual glucose concentration of a person very precisely.

Nevertheless, it would be desirable to improve the accuracy and reliability of the analysis results even further.

SUMMARY OF THE INVENTION

An object underlying the present invention is to provide an apparatus and method for analyzing a material as set forth above that allow for improving the accuracy or reliability of the analysis results.

According to one aspect of the invention, this problem is solved in that a protrusion is provided, said protrusion having a front surface facing said material and being in contact with the material when the material is brought in contact with the contact surface, and in that said excitation radiation is irradiated into the material through said front surface of said protrusion.

Herein, the protrusion may be formed on the contact surface of the measurement body.

In alternative embodiments, the measurement body itself may form the protrusion, or form a part of said protrusion. In this case, the contact surface of the measurement body at the same time forms said front surface of said protrusion, or at least a part of said front surface of said protrusion, and is elevated with respect to a surrounding structure. The surrounding structure can for example be wall parts of a housing of the apparatus or the like.

The inventors have noticed that one critical aspect of the measurement procedure carried out by the apparatus is a reliable and consistent transmission of the excitation radiation into the material. In some of the apparatus described by the present applicant in the prior applications cited above, excitation radiation was guided through the measurement body such as to enter the material at the interface between the contact surface of the measurement body and the material, and it was seen that at this interface, indeed the excitation radiation could generally be coupled very well into the material. This has been found to be particularly true in applications where the material was formed by a fingertip of a user, and where the apparatus was used for measuring the glucose content in the skin. In this case, the fingertip was placed firmly on the contact surface of the measurement body, thereby establishing sufficient optical coupling to allow the excitation radiation to enter the material through the contact surface of the measurement body.

However, extensive research has shown that imperfect and especially unstable optical coupling can be a source of inaccuracy of the measurement. In particular, the inventors noticed that the optical coupling may change during the course of a single measurement, i.e. without intentionally moving the fingertip on or even off the contact surface. If the optical coupling changes during the course of the measurement, this leads to a variation of the intensity of the excitation radiation actually absorbed by the analyte, and hence to a change in the response signal which change is unrelated to the absorptivity of the analyte at the excitation radiation wavelength or the analyte concentration. In other words, loss of optical coupling during part of the measurement could be misinterpreted as reduced absorptivity at the given excitation wavelength. Assessing the analyte spectrum typically involves measuring the absorption at a plurality of characteristic wavelengths, for example wavelengths corresponding to peaks or local absorption minima of the analyte absorption spectrum, and further involves mathematical combinations of response signals associated with different wavelengths, for example subtracting a response signal obtained at a local minimum of the absorption spectrum from that of an absorption peak. It is therefore understandable that in case the optical coupling and hence the effective intensity of the excitation radiation in the material changes between measurements are different wavelengths, or even during a measurement at a certain wavelength, artefacts and inaccuracies in the measurement results may occur.

It was not obvious for the inventors that an unstable optical coupling would be a significant source of error, and it is even less apparent precisely why the optical coupling between the contact surface and the material should significantly change during the measurement, since the fingertip is not intentionally moved for the duration of the measurement. One possible cause could be that the user inadvertently fails to keep the contact pressure between the finger and the contact surface constant. Another possible cause could be that the user inadvertently moves the fingertip slightly on the contact surface, and that a very small movement could have unexpectedly large effects. This could for example be the case where the fingertip moves between a position where the excitation radiation enters the skin at an epidermal ridge of the fingertip and a position where it enters the skin at a position between two epidermal ridges, where reduced optical coupling may occur.

Irrespectively of the precise underlying reasons, the inventors noticed that the optical contact and its consistency can be improved if a protrusion is formed on the contact surface, said protrusion having a front surface facing the material and being in contact with the material when the material is brought in contact with the contact surface, and if the excitation radiation is irradiated into the material through said front surface of said protrusion. Namely, at the front surface of the protrusion, the local contact pressure is found to be significantly higher than on a flat contact surface if the same total force is applied by the finger against the contact surface. This local increase in contact pressure allows for a better optical coupling, and in particular, a more consistent optical coupling during the course of the measurement.

Note that the protrusion does not only allow for an improved optical coupling, but also for an improved thermal or pressure transmitting coupling. Accordingly, the protrusion will also in many cases promote an improved transfer of heat or pressure waves generated by absorption of excitation radiation in the material to be transferred to the measurement body. While not an embodiment of the presently claimed invention, it is also considered herein to use such a protrusion even if the excitation radiation is not irradiated into the material through the front surface thereof.

In a preferred embodiment, the front surface is flat. However, the invention is not limited to this, and particularly in cases where the detection relies on a reflected detection beam, as will be described below, a curved front surface may also be of advantage.

In a preferred embodiment, said protrusion has a footprint area of less than 0.3 cm$^2$, preferably less than 0.2 cm$^2$, more preferably less than 0.1 cm$^2$, even more preferably less than 0.05 cm$^2$ and most preferably less than 0.02 cm$^2$.

In a preferred embodiment, said protrusion has a tapering shape with one or more sidewalls tapering towards said front surface. This tapering shape implies that the front surface may be smaller than the footprint area, and hence leads to an even higher local contact pressure. The tapering sidewalls also add to the stability of the protrusion. Moreover, in some embodiments, where the detection relies on a reflected detection beam, the tapering sidewalls make it easier for the detection light beam to enter the protrusion while keeping the contact surface small, as will be apparent from the description of detailed embodiments below.

In some embodiments, said protrusion has a footprint which is of circular, oval, or square shape.

In particularly preferred embodiments, the protrusion is ridge shaped, having a longer extension in a first direction and a shorter extension in a second direction orthogonal to the first direction, wherein the longer extension exceeds the shorter extension by a factor of at least 1.5, preferably of at least 2.0, more preferably of at least 2.5, and most preferably of at least 3.0. Herein, the expression that "the longer extension exceeds the shorter extension by a factor of at least 1.5" would mean that if the shorter extension was 2 mm, the longer extension would be at least 3 mm.

In a preferred embodiment, said measurement body forming said protrusion or said part of said protrusion is received in a frame or receptacle, wherein said contact surface of said measurement body protrudes from said frame or receptacle, or a wherein said frame or receptacle protrudes from a surrounding structure.

In a preferred embodiment, a pressure sensor is provided for measuring the contact pressure between the material and the measurement body. Herein, the apparatus preferably further comprises a control system configured for receiving signals from said pressure sensor indicating the contact pressure between the material and the measurement body, wherein said control system is configured to check whether said contact pressure is below a predetermined threshold value. In case it is found that the contact pressure is below said threshold value, the control system is configured to one or more of indicate lack of contact pressure to a user, prevent an analyte measurement process from starting, and interrupt a current analyte measurement process.

In other words, while the protrusion helps for establishing high contact pressure precisely where it is needed, i.e. at the front surface where the excitation radiation is coupled into the material, the reliability can be even further improved if the contact pressure is monitored, and if insufficient contact pressure is indicated to the user, such that it can be corrected. Moreover, by preventing the analyte measurement process from starting, or interrupting an analyte measurement process that is already underway, it can be avoided that incorrect measurement results are obtained in case of insufficient contact pressure.

In a preferred embodiment, said apparatus further comprises a clamping device, said clamping device comprising a clamping member movable between an open position in which the clamping member is moved away from the contact surface of the measurement body, and a closed position, in which it is close to said contact surface, said clamping member being biased towards the closed position. The material can be placed on the contact surface when the clamping member is in the open position, and said clamping member is suitable for pressing said material against the contact surface due to the biasing force towards the closed position. This way, a predefined contact pressure can be ensured.

In a preferred embodiment, the aforementioned pressure sensor is arranged on said clamping device. While in the preferred embodiment, the clamping device is combined with the protrusion on the contact surface/formed at least in part by said measurement body, it is also possible to employ it in embodiments without such protrusion.

In a further embodiment, the apparatus further comprises a strap for fixing the material against the contact surface of the measurement body.

In a preferred embodiment, said measurement body is transparent for said excitation radiation, wherein said excitation radiation source is configured for providing said excitation radiation as an excitation beam. Moreover, the excitation radiation source is arranged such that said excitation beam is irradiated into said measurement body at an entrance surface thereof, propagates through a portion of said measurement body and exits from the measurement body at said contact surface. In previous apparatus, the applicant ensured that the excitation radiation beam impinges onto the entrance surface at an angle of 90°, such as to avoid refraction and excess reflection of the excitation radiation beam at the entrance surface. However, extensive research has revealed that a further cause of inadvertent variation of the excitation radiation actually reaching the material is a possible interference of the excitation radiation emitted from the excitation radiation source with excitation radiation that is reflected back from the entrance surface of the measurement body. This interference indeed was found to lead to fluctuations in the intensity of excitation radiation in the material, and to hence immediately lead to variations in the response signals that is unrelated to the analyte concentration. Moreover, the inventors found that by slightly tilting the angle of incidence of the excitation beam, this effect can be suppressed, and the accuracy and reliability of the measurement can be improved. Accordingly, in this embodiment, the excitation beam is directed to impinge on the entrance surface at an angle of 89.0° or less, preferably 88.0° or less, and most preferably 87.5° or less. This way, the inadvertent interference can be reliably prevented. A further advantageous effect of this is that it can be prevented that excitation radiation is reflected back into the excitation radiation source which could possibly be damaged by it. On the other hand, the angle of incidence should not deviate too much from 90°, such as to avoid losses due to excessive reflection. Accordingly, in this embodiment, the angle of incidence should be 82.0° or more, preferably 84.0° or more and most preferably 85.0° or more. While this embodiment is advantageously used together with the protrusion on the contact surface/formed at least in part by said measurement body, it is also possible to employ it in embodiments without such protrusion.

In a preferred embodiment, said excitation beam impinges on the contact surface of the measurement body at an angle of 90°±1.5°, to thereby keep losses due to reflection at the contact surface to a minimum.

In a preferred embodiment, the entrance surface and the contact surface at the respective portions thereof where the excitation beam enters and leaves the measurement body, respectively, are inclined with respect to each other with an angle of 1.0° or more, preferably 2.0° or more, and most preferably 2.5° or more, and 8.0° or less, preferably 6.0° or less and most preferably 5.0° or less. Graphically speaking, the measurement body according to this embodiment may have a slightly "wedge-like" shape, which allows for establishing both, the slight inclination of the excitation beam at the entrance surface and the orthogonal orientation thereof at the contact surface.

In a preferred embodiment, said detection device comprises a light source for generating a detection light beam travelling through at least a portion of said measurement body or a component included in said measurement body. Herein, said physical response of the measurement body to heat or pressure waves received from said material upon absorption of said excitation radiation is a local change in the refractive index of said measurement body or said component, and said detection device is configured for detecting one of a change in the light path or a change in the phase of detection beam due to said change in refractive index.

In a preferred embodiment, said detection device is configured such that said detection light beam is irradiated into the measurement body at an entrance surface, wherein said detection light beam impinges on the entrance surface at an angle of incidence with respect to said entrance surface of 89° or less, preferably 88° or less, and most preferably 87.5° or less, and of 80° or more, preferably 82° or more, more preferably 84° or more and most preferably 85° or more. This way, it can be avoided that the detection light beam is reflected back onto itself, which may lead to interference and undesirable interference phenomenon. A further advantageous effect of this is that it can be prevented that detection light beam is reflected back into the detection light source which could possibly be damaged thereby.

In a preferred embodiment, said measurement body is received in a frame or receptacle that allows for turning said measurement body such as to adjust said angle of incidence of said detection light beam when impinging on said entrance surface of said measurement body. This way, adjusting the proper angle of incidence of the detection light beam onto the measurement body is greatly facilitated, as compared to, for example adjusting the detection light source or any optical elements such as mirrors in the light path of the detection light beam. Preferably, said frame or receptacle allows for turning said measurement body around an axis parallel with the excitation light beam, or deviating from parallel by less than 10°, preferably less than 5°. In the most preferred embodiments, said turning axis of said measurement body coincides with said excitation light beam.

In a related embodiment, said measurement body is transparent for said detection light beam, said detection light beam is directed to be totally or partially reflected at a surface of said measurement body that is in thermal or pressure-transmitting contact with said material, wherein said detection device comprises a detector for detecting a degree of deflection, in particular a deflection angle, of the detection light beam after its reflection at said contact surface, due to said local change in refractive index. Herein, said detection device preferably comprises a photodetector, in particular a position sensitive photodetector.

In this embodiment, said detection light beam is preferably directed to be totally or partially reflected at said front surface of said protrusion that is in thermal or pressure-transmitting contact with said material. In other words, in this embodiment, the detection light beam is reflected at the same surface through which the excitation radiation exits the measurement body and enters into the material. This implies that the detection light beam is reflected in an area where a comparatively large local change in refractive index due to heat or pressure waves received from the material upon absorption of the excitation radiation can be expected, which in turn implies that the deflection of the detection light beam due to said local change in refractive index is expected to be comparatively large.

Note that the concept of the detection light beam being "deflected" relates to the total change in angle or change in impingement position at the detector, or in other words, how the detected position of the detection light beam differs from its position without excitation of and absorption by the material. This "deflection" is hence the accumulated effect that the local change of refractive index has on the detection light beam along its light path. A closer inspection reveals that in many cases, part of the deflection of the light beam due to the local change in refractive index occurs before the detection light beam is reflected at a surface of the measurement body that is in thermal or pressure-transmitting contact with the material, which in this case is formed by the front surface of the protrusion. Accordingly, the local change in refractive index typically also leads to a shift of the location precisely where on the surface the detection light beam will be reflected.

In view of this understanding, in a preferred embodiment, the front surface of the protrusion is curved in at least one principal direction. This curvature implies that said change in location where the detection light beam is reflected is also accompanied by a change of angle of incidence, and hence leads to a corresponding change in the angle of reflection as well.

Accordingly, using a curved reflection surface, the total deflection assessed by the detection device, such as the shift in position detected with a position sensitive detector, can be increased.

In a preferred embodiment, said curvature in said at least one principal direction corresponds to a radius of curvature in a range of 5 to 30 mm, preferably 10 to 20 mm.

In a preferred embodiment, said curvature in said at least one principal direction is one of concave or convex.

In a preferred embodiment, the detection light beam prior to and after reflection at said front surface define a detection light plane, and said at least one principal direction lies within said detection light plane or forms an angle with the detection light plane that is less than 30°, preferably less than 20°. This way, it is ensured that the predominant effect of the curvature on the deflection is in the detection light plane.

Note that in cases where a detection light beam is to be reflected at the front surface of the protrusion, the geometry of the protrusion generally restricts the possible angles of inclination of the detection light beam with respect to the contact surface. For example, if the protrusion has a height h and a circular footprint with a radius r, the inclination angle $\alpha$ of the detection light beam with respect to the contact surface must obey the condition $\tan(\alpha) > h/r$ such as to "fit" into the protrusion. From a different perspective, given a desired height h of the protrusion and a desired angle $\alpha$, one has to face a lower boundary of the radius r, or in other words, a lower boundary of the footprint size. As was explained above, by using one or more tapering sidewalls, the size of the front surface of the protrusion can be reduced over that of the footprint, to thereby allow for smaller front surfaces and hence higher contact pressure even for larger footprint areas.

A further improvement can be made in a preferred embodiment, in which the protrusion is ridge-shaped, having a longer extension in a first direction and a shorter extension in a second direction orthogonal to the first direction, wherein the longer extension exceeds the shorter extension by a factor of at least 1.5, preferably of at least 2.0, more preferably of at least 2.5, and most preferably of at least 3.0, and said first direction is parallel with said detection light plane, or forms an angle with the detection light plane that is less than 30°, preferably less than 20°. In other words, according to this embodiment, the detection light plane corresponds at least approximately to the long direction of the ridge-shaped protrusion, meaning that at a given height of the protrusion, the angle of inclination of the detection light beam onto the front surface of the protrusion may be smaller. At the same time, with this orientation of the detection light plane, the extension in the second, short direction of the ridge-shaped protrusion is generally independent of the inclination angle, and can hence be chosen comparatively small, to thereby decrease the size of the front surface and allow for higher contact pressure at the front surface.

In a preferred embodiment, the detection light source is arranged such that said detection light beam is irradiated into said measurement body at an entrance surface, propagates through a portion of said measurement body and exits from the measurement body at an exit surface, wherein the detection beam—in absence of any deflection due to said local change in refractive index—impinges on the exit surface at an angle of 5° or more, preferably 10° or more and most preferably 150 or more with respect to the normal to the exit surface, such that the detection beam is refracted upon exiting from the exit surface of the measurement body, wherein the orientation of the exit surface with respect to the detection light beam is such that said deflection of the detection light beam in response to said heat or pressure waves being transferred to said measurement body increases said angle of said detection light beam with respect to the normal to the exit surface.

In previous designs of the applicant, the shape of the measurement body was generally chosen such that the detection beam would be perpendicular to the entrance and exit surfaces, to avoid losses due to reflection and to avoid refraction, which at first sight would only make the optical setup more complicated. However, according to this embodiment, the detection light source is arranged such that the detection light beam is deliberately refracted at least at the exit surface in a manner defined above. Since usually, the refractive index of the measurement body will be higher than that of the surrounding, an increase in the angle of the detection light beam to the normal to the exit surface will lead to an even larger increase in the angle of the refracted light beam, such that the deflection of the light beam as detected at the detection device is further increased, thereby leading to a larger response signal. This way, the signal-to-noise ratio can be increased. The effect will generally be larger, the more the angle of incidence of the detection beam deviates from the normal to the exit surface. However, it has to be of course avoided that the "critical" angle of total reflection is ever reached. Moreover, for angles close to this critical angle, the proportion of light of the detection light beam reflected at said exit surface will increase, thereby attenuating the intensity of the refracted detection light beam that actually reaches the detection device, such as a photodetector. Accordingly, the best choice for the angle of incidence may be a compromise between a larger degree of refraction and sufficient intensity of the refracted detection light beam. At any rate, the deviation of the angle of incidence from the normal to the axis surface should be at least 5°, and it is preferably at least 10° and most preferably at least 15°. While this embodiment is advantageously used together with the protrusion on the contact surface/formed at least in part by said measurement body, it is also possible to employ it in embodiments without such protrusion.

In a preferred embodiment, the detection light source is arranged such that said detection light beam is irradiated into said measurement body at an entrance surface, propagates through a portion of said measurement body and exits from the measurement body at an exit surface, wherein a focusing lens is attached to or formed integrally with the entrance surface for focusing said detection light beam entering into said measurement body in at least one dimension and/or a collimating lens is attached to or formed integrally with the exit surface for collimating said detection light beam in at least one dimension.

The inventors have noticed that the quality of the measurement is improved if the detection light beam is focused when it is reflected on the contact surface, which is also the area where it will interact with a thermal lens formed in the measurement body. For a clear characteristic deflection, it is advantageous if the diameter of the detection beam in this area is comparatively small, which can be achieved with said focusing lens. In other words, the purpose of the focusing lens is not necessarily to truly focus the detection light beam at some focal point, but rather to reduce its diameter at least in the area where it interacts with the thermal lens. However, this focusing implies that the detection light beam spreads out on its way towards the detection device. This is usually not of much concern if the detection device, such as a position sensitive detector, is arranged directly adjacent or at least close to the exit surface of the detection beam. However, the inventors found out that the signal-to-noise ratio of the measurement can be further increased if the distance between the exit surface and the detector is increased, as this will lead to a larger degree of deflection, for example manifested by a larger shift of the position where the detection light beam impinges on a position sensitive detector. Note that herein, the "larger degree of deflection" does not relate to a larger deflection angle, which would be one possible meaning of "degree of deflection", but a larger effect of the deflection as detected by the detection device. For example, the distance between the reflection at the contact surface of the measurement body and the detection at the detection device may be at least 4 cm, in some embodiments even 9 cm or more, thereby introducing a sort of leverage to the deflection as detected by the detection device. However, when the detection device is located at an appreciable distance from the exit surface, it is advantageous if the detection light beam is collimated after exiting the measurement body, to keep the diameter of the detection beam constant. It is nevertheless emphasized that it is not always necessary that the focusing and the collimation is done in both dimensions, in many practical applications, a certain spread in one of the directions can even be desired, as will be explained below. Accordingly, the focusing lens and/or other collimating lens have to be effective only at least in one dimension. Indeed, in preferred embodiments, at least one of said focusing lens and said collimating lens is a cylinder lens focusing and collimating the detection light beam at least predominantly in one dimension, respectively.

Moreover, by attaching the focusing lens and/or the collimating lens to the measurement body, or by even more preferably forming them integrally with it, no separate adjustment of these lenses during assembly of the apparatus or even during use of the apparatus is necessary. While this embodiment is advantageously used together with the protrusion on the contact surface/formed at least in part by said measurement body, it is also possible to employ it in embodiments without such protrusion.

In a preferred embodiment, said detector comprises a position sensitive detector on which said detection light beam impinges, wherein said position sensitive detector is sensitive for detecting shifts in position of the detection light beam impinging thereon in at least one sensing direction. Moreover, said position sensitive detector is arranged such that said deflection of said detection light beam leads to a shift of the position of the detection light beam impinging thereon in said at least one sensing direction. Finally, a cylinder lens is provided in the light path of the detection light beam for shaping the profile of the detection light beam such that the diameter of the detection light beam impinging on said position sensitive detector in said sensing direction is at least 1.5 times as large, preferably at least 2.0 times as large as the diameter of the detection light beam in a direction orthogonal to said sensing direction. The inventors noticed that when using a position sensitive detector that is sensitive for detecting shifts in the position of the detection light beam impinging thereon in at least one sensing direction, the signal-to-noise ratio, and in some embodiments, the linearity of the sensor output, can be increased if the beam profile is such that the light spot formed on the position sensitive detector is elongate in the sensing direction in the manner defined above. This is particularly true for position sensitive detectors measuring current differences at their respective ends. The elongate shape of the light spot according to this aspect of the invention is established using such cylinder lens. While this embodiment is advantageously used together with the protrusion on the contact surface/formed at least in part by said measurement body, it is also possible to employ it in embodiments without such protrusion.

In a preferred embodiment, said cylinder lens is a collimating lens arranged in said light path of the detection light beam between its reflection at said contact surface and said position sensitive detector, wherein said cylinder lens is arranged to collimate said detection light beam at least predominantly (but possibly exclusively) in a dimension orthogonal to said sensing direction of said position sensitive detector, wherein said cylindrical collimating lens is preferably formed integrally with an exit surface of said measurement body at which the detection light beam exits from the measurement body.

In addition or alternatively, the position sensitive detector may be arranged at an angle deviating from 90° from the detection light beam, such that due to this angle, an elongate light spot is formed on the position sensitive detector having its larger extension in the sensing direction.

In a preferred embodiment, the apparatus further comprises a beam splitter for splitting a source light beam into said detection light beam and a reference light beam, wherein said reference light beam is likewise directed to be totally or partially reflected at a surface of said measurement body that is in thermal or pressure-transmitting contact with said material, but in a region where any effect of heat or pressure waves received from the material upon absorption of excitation radiation is negligible. Moreover, said apparatus comprises a further detection device for detecting a degree of deflection, in particular a deflection angle, of the reference light beam after its reflection at said contact surface, wherein said detection device preferably comprises a photodetector, in particular a position sensitive photodetector.

This reference light beam is exposed to the same types of external influences as the detection light beam, except for the heat or pressure waves due to absorption of excitation radiation. Accordingly, by measuring possible deflections of the reference light beam, these external influences can be accounted for and removed from the measurement results obtained with the detection light beam. While in the preferred embodiment, the additional reference beam is combined with the protrusion on the contact surface/formed at least in part by said measurement body, it is also possible to employ it in embodiments without such protrusion.

In an alternative preferred embodiment said detection device comprises an interferometric device allowing for assessing said change in phase of the detection beam and generating a response signal indicative of said change in phase.

In a yet further alternative embodiment, said measurement body or a component in said measurement body has electrical properties that change in response to a local change in temperature or a change in pressure associated therewith, wherein said detection device comprises electrodes for capturing electrical signals representing said electrical properties.

In a yet further embodiment, the apparatus comprises a fiber embedded in said measurement body, a detection light source provided at one end of said fiber for coupling detection light into said fiber and a mode detector provided at the other end of said fiber. The mode detector is suitable for detecting changes in optical modes of said detection light in response to the heat or pressure waves received by the measurement body from said material. For example, the mode detector could comprise a camera suitable for visualising the modes, typically an interference pattern of several modes, as well as a processor configured for detecting changes in the modes based on an image analysis of the camera images. The processor could be a dedicated processor associated with the mode detector, or could be provided by the control system of the apparatus described above. Detectable changes in optical modes may comprise a shift or a rotation of an interference pattern of optical modes at the mode detector. The distance of the shift or a rotation angle is hence a quantitative parameter that is associated with the amount of heat or intensity of a pressure wave received from the material, and hence ultimately indicative of the amount of excitation light absorbed by the material. Note that such a change in the interference pattern of the modes can be readily detected using a camera or image sensor, but other devices are likewise possible, for example sensors or detectors allowing for measuring some sort of space resolved intensity values, without necessarily providing a full image. In this embodiment, the "physical response" would be a transient change of the optical properties of the fiber due to the received heat or pressure wave, and the "response signal" would be the detectable change in the optical modes, such as a change in an interference pattern of several modes. While in the preferred embodiment, this type of mode detection is combined with the protrusion on the contact surface/formed at least in part by said measurement body, it is also possible to employ it in embodiments without such protrusion.

In preferred embodiments, said material is human tissue, in particular human skin, and said analyte is glucose present in the skin, in particular in the interstitial fluid thereof.

In preferred embodiments, said excitation radiation is generated using an array of lasers, in particular quantum cascade lasers, each having a dedicated wavelength.

In alternative preferred embodiments, said excitation radiation is generated using at least one tunable laser, in particular at least one tunable quantum cascade laser.

In a preferred embodiment, some or all of said excitation wavelengths are in a range of 5 μm to 13 μm, preferably 8 μm to 11 μm. In alternative embodiments, some or all of said excitation wavelengths are in a range of 3 μm to 5 μm. This wavelength range is for example useful for detecting absorption of $CH_2$ and $CH_3$ vibrations in fatty acids.

A further aspect of the present invention relates to a method for analyzing a material comprising at least one analyte, said method comprising bringing a measurement body having a contact surface in thermal contact or pressure-transmitting contact with said material, said thermal or pressure-transmitting contact permitting heat or pressure waves generated by absorption of excitation radiation in the material to be transferred to said measurement body, irradiating excitation radiation into the material to be absorbed therein, and detecting a physical response of the measurement body, or of a component included therein, to heat or a pressure wave received from said material upon absorption of said excitation radiation and generating a response signal based on said detected physical response, said response signal being indicative of the degree of absorption of excitation radiation, characterized in that a protrusion is provided, said protrusion having a front surface facing said material and being in contact with the material when the material is brought in contact with the contact surface, and in that said excitation radiation is irradiated into the material through said front surface of said protrusion, wherein said protrusion is formed on said contact surface of said measurement body, or wherein said measurement body forms said protrusion or a part of said protrusion, in which the contact surface of said measurement body forms said front surface of said protrusion and is elevated with respect to a surrounding structure.

In a preferred embodiment of the method, said front surface is flat.

In a preferred embodiment of the method, said protrusion has a footprint area of less than 0.3 cm², preferably less than 0.2 cm², more preferably less than 0.1 cm², even more preferably less than 0.05 cm² and most preferably less than 0.02 cm².

In a preferred embodiment of the method, said protrusion has a tapering shape with one or more sidewalls tapering towards said front surface.

In a preferred embodiment of the method, said protrusion has a footprint which is of circular, oval, or square shape.

In a preferred embodiment of the method, the protrusion is ridge shaped, having a longer extension in a first direction and a shorter extension in a second direction orthogonal to the first direction, wherein the longer extension exceeds the shorter extension by a factor of at least 1.5, preferably of at least 2.0, more preferably of at least 2.5, and most preferably of at least 3.0.

In a preferred embodiment of the method, the contact pressure between the material and the measurement body is measured.

Preferably, the method further comprises a step of checking whether said contact pressure is below a predetermined threshold value, and in case it is found that the contact pressure is below said threshold value, carrying on one or more of the following steps:

indicating lack of contact pressure to a user, preventing an analyte measurement process from starting, and interrupting a current analyte measurement process.

Preferably, the method further comprises a step of fixing said material to the contact surface using a clamping device, said clamping device comprising a clamping member movable between an open position in which the clamping member is moved away from the contact surface of the measurement body, and a closed position, in which it is close to said contact surface, said clamping member being biased towards the closed position, wherein said material is placed on the contact surface when the clamping member is in the open position, and wherein said clamping member presses said material against the contact surface due to the biasing force towards the closed position.

In a preferred embodiment of the method, said pressure sensor is arranged on said clamping device.

In a preferred embodiment, the method comprises a step of fixing said material to the contact surface using a strap.

In a preferred embodiment of the method, said measurement body is transparent for said excitation radiation, wherein said excitation radiation source provides said excitation radiation as an excitation beam, and wherein the excitation beam is irradiated into said measurement body at an entrance surface thereof, propagates through a portion of said measurement body and exits from the measurement body at said contact surface, wherein the excitation beam impinges on the entrance surface at an angle of 89.0° or less, preferably 88.0° or less, and most preferably 87.5° or less, and of 82.0° or more, preferably 84.0° or more and most preferably 85.0° or more.

In a preferred embodiment of the method, said excitation beam impinges on the contact surface of the measurement body at an angle of 90°±1.50.

In a preferred embodiment of the method, the entrance surface and the contact surface at the respective portions thereof where the excitation beam enters and leaves the measurement body, respectively, are inclined with respect to each other with an angle of 1.0° or more, preferably 2.0° or more, and most preferably 2.5° or more, and 8.0° or less, preferably 6.0° or less and most preferably 5.0° or less.

In a preferred embodiment of the method, said detection comprises generating a detection light beam travelling through at least a portion of said measurement body or a component included in said measurement body, said physical response of the measurement body to heat or pressure waves received from said material upon absorption of said excitation radiation is a local change in the refractive index of said measurement body or said component, and said detecting comprises detecting one of a change in the light path or a change in the phase of detection beam due to said change in refractive index.

In a preferred embodiment of the method, said detection light beam is irradiated into the measurement body at an entrance surface such that said detection light beam impinges on the entrance surface at an angle of incidence with respect to said entrance surface of 890 or less, preferably 880 or less, and most preferably 87.5° or less, and of 80° or more, preferably 820 or more, more preferably 840 or more and most preferably 850 or more.

In a related embodiment of said method, said measurement body is received in a frame or receptacle that allows for turning said measurement body such as to adjust said angle of incidence of said detection light beam when impinging on said entrance surface of said measurement body, wherein in particular, said frame or receptacle allows for turning said measurement body around an axis parallel with the excitation light beam, or deviating from parallel by less than 10°, preferably less than 5°, wherein most preferably, said axis turning axis of said measurement body coincides with said excitation light beam.

In a preferred embodiment of the method, said measurement body is transparent for said detection light beam, said detection light beam is directed to be totally or partially reflected at a surface of said measurement body that is in thermal or pressure-transmitting contact with said material, and wherein said detection comprises detecting a degree of deflection, in particular a deflection angle, of the detection light beam after its reflection at said contact surface, due to said local change in refractive index, wherein said detection is preferably carried out using a photodetector, in particular a position sensitive photodetector.

In a preferred embodiment of the method, said detection light beam is directed to be totally or partially reflected at said front surface of said protrusion that is in thermal or pressure-transmitting contact with said material.

In a preferred embodiment of the method, the front surface of the protrusion is curved in at least one principal direction. Herein, said curvature in said at least one principal direction corresponds to a radius of curvature in a range of 5 to 30 mm, preferably 10 to 20 mm. Said curvature in said at least one principal direction is one of concave or convex.

In a preferred embodiment of the method, the detection light beam prior to and after reflection at said front surface defines a detection light plane, and said at least one principal direction lies within said detection light plane or forms an angle with the detection light plane that is less than 30°, preferably less than 20°.

In a preferred embodiment of the method, the detection light beam prior and after reflection at said front surface defines a detection light plane, and said first direction is parallel with said detection light plane or forms an angle with the detection light plane that is less than 30°, preferably less than 20°.

In a preferred embodiment of the method, the detection light source is arranged such that said detection light beam is irradiated into said measurement body at an entrance surface, propagates through a portion of said measurement body and exits from the measurement body at an exit surface, wherein the detection beam impinges—in absence of any deflection due to said local change in refractive index—on the exit surface at an angle of 5° or more, preferably 10° or more and most preferably 150 or more with respect to the normal to the exit surface, such that the detection beam is refracted upon exiting from the exit surface of the measurement body, wherein the orientation of the exit surface with respect to the detection light beam is such that said deflection of the detection light beam in response to said heat or pressure waves being transferred to said measurement body increases said angle of said detection light beam to the normal to the exit surface.

In a preferred embodiment of the method, said detection light beam is irradiated into said measurement body at an entrance surface, propagates through a portion of said measurement body and exits from the measurement body at an exit surface, wherein a focusing lens is formed integrally with the entrance surface for focusing said detection light beam entering into said measurement body in at least one dimension and/or a collimating lens is formed integrally with the exit surface for collimating said detection light beam in at least one dimension. Herein, at least one of said focusing lens and said collimating lens is preferably a cylinder lens focusing and collimating the detection light beam at least predominantly in one dimension, respectively.

In a preferred embodiment of the method, said detector comprises a position sensitive detector on which said detection light beam impinges, wherein said position sensitive detector detects shifts in position of the detection light beam impinging thereon in at least one sensing direction, wherein said position sensitive detector is arranged such that said deflection of said detection light beam leads to a shift of the position of the detection light beam impinging thereon in said at least one sensing direction, and wherein a cylinder lens is provided in the light path of the detection light beam for shaping the profile of the detection light beam and/or the position sensitive detector is arranged at an angle deviating from 90° from the detection light beam, such that the diameter of the detection light beam impinging on said position sensitive detector in said sensing direction is at least 1.5 times as large, preferably at least 2.0 times as large as the diameter of the detection light beam in a direction orthogonal to said sensing direction.

In a preferred embodiment of the method, said cylinder lens is a collimating lens arranged in said light path of the detection light beam between its reflection at said contact surface and said position sensitive detector, wherein said cylinder lens collimates said detection light beam at least predominantly in a dimension orthogonal to said sensing direction of said position sensitive detector, wherein said cylinder collimating lens is preferably formed integrally with an exit surface of said measurement body at which the detection light beam exits from the measurement body.

In a preferred embodiment of the method, a source light beam is splitted into said detection light beam and a reference light beam, wherein said reference light beam is likewise directed to be totally or partially reflected at a surface of said measurement body that is in thermal or pressure-transmitting contact with said material, but in a region where any effect of heat or pressure waves received from the material upon absorption of excitation radiation is negligible, and wherein a degree of deflection, in particular a deflection angle, of the reference light beam after its reflection at said contact surface is detected, preferably using a photodetector, in particular a position sensitive photodetector.

In a preferred embodiment of the method, said detection comprises using an interferometric device allowing for assessing said change in phase of the detection beam and generating a response signal indicative of said change in phase.

In a preferred embodiment of the method, said measurement body or a component in said measurement body has electrical properties that change in response to a local change in temperature or a change in pressure associated therewith, and wherein said detection device comprises electrodes for capturing electrical signals representing said electrical properties.

In a preferred embodiment of the method, an optical fiber is embedded in said measurement body, a detection light source is provided at one end of said fiber for coupling detection light into said optical fiber and a mode detector is provided at the other end of said fiber, wherein using said mode detector, changes in optical modes of said detection light in response to the heat or pressure waves received by the measurement body from said material are detected, wherein said changes in optical modes preferably comprise a shift or a rotation of an interference pattern of optical modes at the mode detector.

In a preferred embodiment of the method, said material is human tissue, in particular human skin, and said analyte is glucose present in the skin, in particular in the interstitial fluid thereof.

Preferably, the method further comprises a step of generating said excitation radiation using an array of lasers, in particular quantum cascade lasers, each having a dedicated wavelength.

Preferably, the method further comprises a step of generating said excitation radiation using at least one tunable laser, in particular at least one tunable quantum cascade laser.

In a preferred embodiment of the method, some or all of said excitation wavelengths are in a range of 5 μm to 13 μm, preferably 8 μm to 11 μm.

SHORT DESCRIPTION OF THE FIGURES

DESCRIPTION OF THE PREFERRED EMBODIMENTS

It is to be understood that both the foregoing general description and the following description are exemplary and explanatory only and are not restrictive of the methods and devices described herein. In this application, the use of the singular may include the plural unless specifically stated otherwise. Also, the use of "or" means "and/or" where applicable or unless stated otherwise. Those of ordinary skill in the art will realize that the following description is illustrative only and is not intended to be in any way limiting. Other embodiments will readily suggest themselves to such skilled persons having the benefit of this disclosure. Reference will now be made in detail to various implementations of the example embodiments as illustrated in the accompanying drawings. The same reference signs will be used to the extent possible throughout the drawings and the following description to refer to the same or like items.

Figure 1:
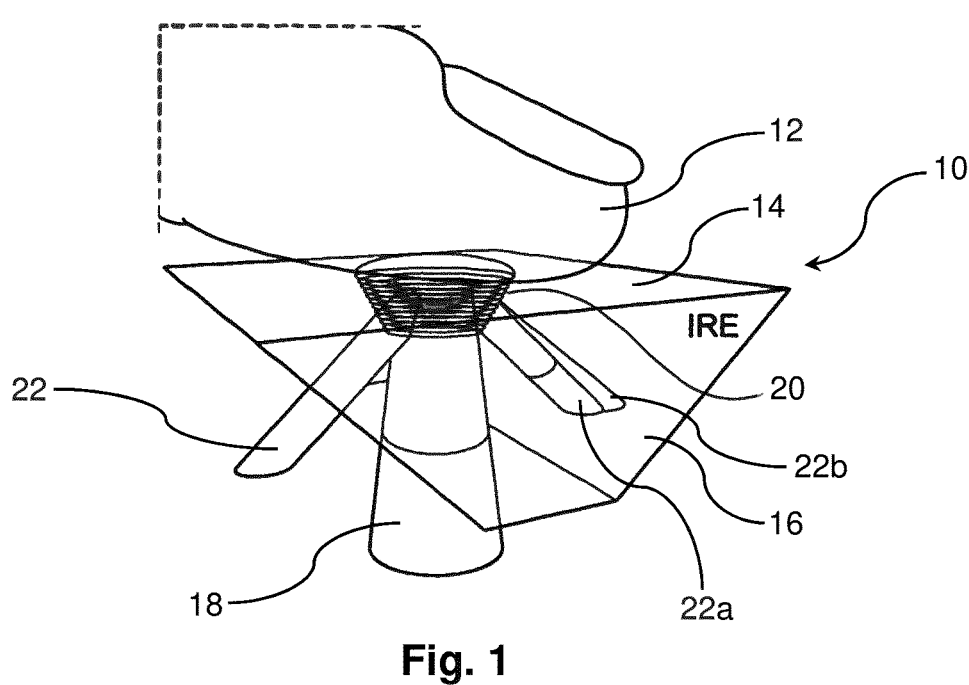
FIG. 1 is a schematic illustration of the measurement principle underlying some embodiments of the invention.

FIG. 1 is a schematic illustration of the measurement principle underlying the analyte measurement procedure summarized above and described in more detail in the following. While the method and apparatus of the invention are suitable for analyzing various materials comprising at least one analyte, the following description will focus on specific embodiments where the material is the skin of a patient and the analyte is glucose within the interstitial fluid of the skin. It is to be understood that all details and explanations given in the following with specific reference to glucose measurement are considered in relation to other materials and analytes as well, where applicable, without explicit mention in the following.

Figure 2:
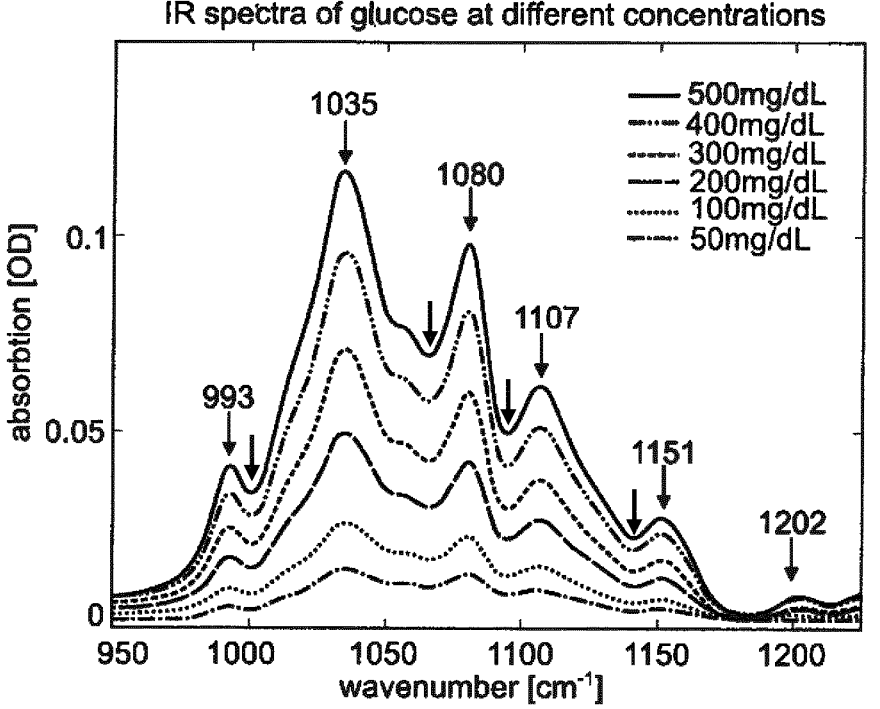
FIG. 2 shows the absorption spectrum of the glucose in water, with the water background subtracted.

In the illustration of FIG. 1, a fingertip 12 of a user is brought in thermal contact with a contact surface 14 of a measurement body 16. In an alternative implementation, which is not shown, the fingertip may be coupled acoustically to the measurement body through an acoustic cell which may include a hollow space filled with a liquid or gas allowing for a transfer of pressure waves to the measurement body. An excitation beam 18 is irradiated to the measurement body 16 through air or through a waveguide (not shown) and then through the measurement body 16 and into the skin at the fingertip 12. In order to determine the concentration of the glucose in the skin, in particular in the interstitial fluid of the skin, various wavelengths of the excitation radiation 18 are chosen one after the other or at least partially at the same time for absorption measurement, such that from the measured absorption values the concentration of the glucose can be determined. In FIG. 2, absorption spectra are shown for different concentrations of glucose in water, wherein the contribution of the absorption by water has been subtracted. As is seen therein, the glucose molecule has several characteristic absorption peaks in the mid infrared region at wave numbers ranging between 993 $cm^{-1}$ and 1202 $cm^{-1}$, corresponding to wavelengths ranging from 10.07 µm to 8.32 µm, respectively. In between adjacent absorption peaks, local absorption minima are seen, which are indicated by vertical arrows without wave numbers in FIG. 2. As is apparent from FIG. 2, particularly the difference in absorption at the absorption peaks and the local absorption minima are characteristic for the glucose concentration. Accordingly, in order to be able to determine the glucose concentration, it is preferable to measure the absorption at some or all of the absorption peaks and at some or all of the local absorption minima and potentially also at some point between the maxima and minima. These wavelengths are referred to as a "analyte(glucose)-characteristic-wavelengths" herein. While wavelengths exactly at the absorption peaks or local absorption minima are the preferred choices for the glucose-characteristic wavelengths, wavelengths close to the peaks/local minima but in an individually defined distance from them may also be used. Accordingly, as understood herein, "analyte-characteristic-wavelengths" are also wavelengths where the difference in absorption to that at the closest absorption peak or the closest local absorption minimum is less than 30%, preferably less than 20% of the difference in absorption between the closest absorption peak and closest local absorption minimum.

The intensity of the excitation beam 18 is time modulated with a certain frequency f, such that the excitation radiation, in this case excitation light has alternating intervals of high intensity and low or even vanishing intensity. Without wishing to limit the modulation to any particular waveform, high intensity intervals are referred to as "excitation light pulses" in the following. During the excitation light pulses, excitation light having the glucose-characteristic-wavelength will be absorbed, such that the radiation energy will be converted to heat. Since the glucose molecules relax from the excited state within approximately $10^{-12}$ s, the generation of a corresponding heat pulse and/or pressure wave can be regarded as occurring instantaneously for all practical purposes.

Accordingly, along with the excitation light pulses, local heat pulses are generated at the absorption site, leading to a temperature field that varies as a function of space and time and that could be referred to as a thermal wave. As was explained above, the term thermal "wave" is somewhat misleading, since the travel of heat through the material is not governed by a wave equation, but by a diffusion equation instead. However, the notion of a "heat wave" is correct at least to the extent that heat pulses propagate from within the skin to the surface 14 of the measurement body 16 and into the measurement body 16 similarly to what one is used to from wave propagation. A thermal gradient 20 that is caused by such a heat pulse is schematically shown in FIG. 1.

The heat received by the measurement body 16 from the skin of the finger 12 causes a physical response that can be detected with one of various possible detection devices which are devised for generating a response signal based on the physical response, wherein this response signal is indicative of the degree of absorption of the excitation light. Various ways of detecting the physical response and generating suitable response signals will be described below.

However, irrespective of the precise way of detecting the physical response, it is worth noting that the maximum depth underneath the surface of the skin in which the absorption can be detected by means of heat pulses travelling to the measurement body 16 is found to be limited to a good approximation by the thermal diffusion length $\mu_t$ of the skin, which is defined as $$\mu t(f) = \sqrt{\frac{kt}{\rho \cdot Cp \cdot 2f}}$$

and which depends on the density $\rho$, the specific heat capacity $C_p$, and the thermal conductivity $k_t$ of the material as well as on the modulation frequency f of the excitation light. In other words, by selecting the modulation frequency f, a depth can be defined up to which any absorption of the excitation light is reflected in the heat pulses received at the measurement body 16.

With reference again to FIG. 1, in the embodiment shown, the physical response to the absorption heat received from the skin is a change in refractive index in an area close to the surface 14 of the measurement body 16 where the heat gradient 20 is transiently formed. This local change in refractive index forms what could be regarded as a thermal lens that can be detected by means of a detection light beam 22. The detection beam 22 is passing through the thermal lens or heat gradient region 20 and then reflected at the interface of the measurement body 16 and the skin of the finger 12. Whenever a heat pulse is received from the skin, a local change in refractive index occurs, and this leads to a deflection of the detection beam 22 by the interaction with the material of the measurement body in the region of the thermal lens. In FIG. 1, reference sign 22b corresponds to the non-deflected detection beam 22, whereas reference sign 22a corresponds to the detection beam when it is deflected due to the thermal lens formed in the heat gradient region 20. This deflection can be measured and forms an example of the aforementioned response signal. The degree of the deflection is indicative of the amount of heat received, and hence the degree of absorption of the excitation light 18 in the skin of the finger 12. Herein, the "degree of deflection" may refer to a deflection angle, but more generally corresponds to any deviation between the detection light beams detectable by the corresponding detection device.

Figure 3:
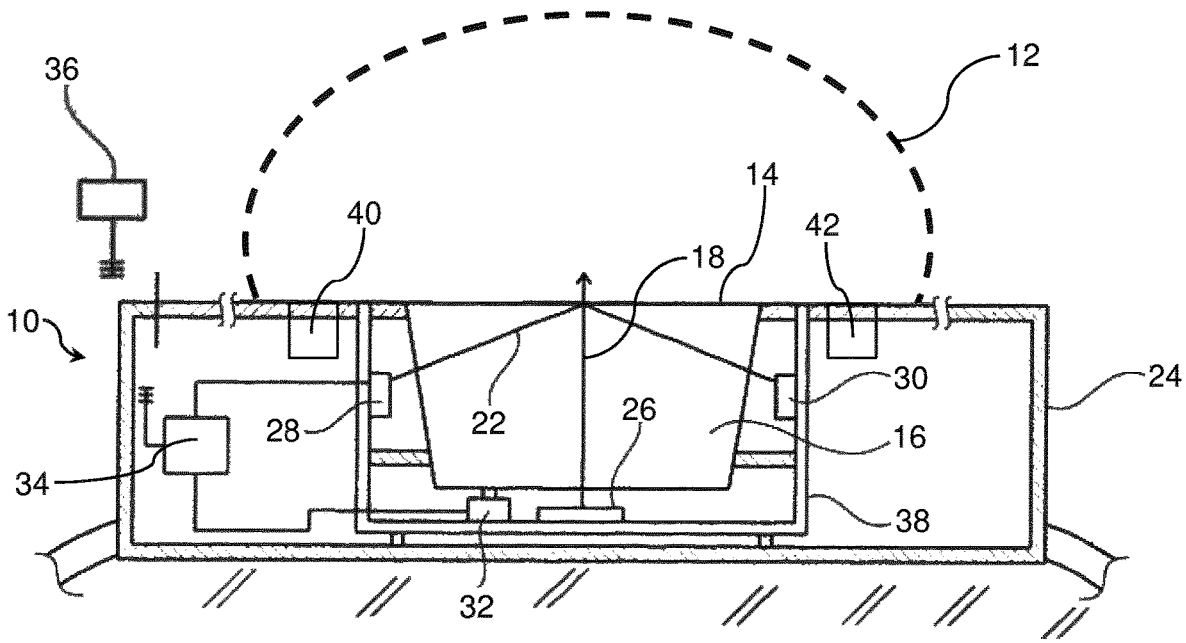
FIG. 3 is a schematic sectional view of an apparatus for analyzing a material relying on response signals based on a deflection of a detection light beam.

FIG. 3 shows a more detailed sectional view of an apparatus 10 that relies on the measurement principle as illustrated with reference to FIG. 1. The apparatus 10 comprises a housing 24 which includes the measurement body 16, having a top surface (contact surface) 14 on which a finger 12 rests. Within the housing 24, an excitation light source 26 is provided, which generates the excitation light beam 18. In the embodiment shown, the excitation light source 26 comprises an array of quantum cascade lasers each having a dedicated wavelength. For example, the array of quantum cascade lasers could include individual quantum cascade laser elements with wavelengths corresponding to the absorption peaks and local minima shown in FIG. 2 (i.e. the glucose-characteristic-wavelengths), as well as other wavelengths that can be used for reference measurements, or for detecting other substances that could be disturbing to the measurement of the glucose, for example lactate or albumin. The laser array may irradiate an excitation beam directly into and through the measurement body 16, but it may as well irradiate into a light waveguide (not shown) which couples the laser array with the measurement body and leads the excitation beam in a curved or non-curved manner to the measurement body 16. A light waveguide may as well be used in the case of generation of the excitation beam by a single tunable laser.

The apparatus 10 further comprises a light source 28, for example a laser, for emitting the detection beam 22, as well as a position-sensitive detector 30 which allows for detecting the deflection of the detection light beam 22. Note that as understood herein, the term "light beam" is not restricted to light in the visible range, although in preferred embodiments, the detection light beam 22 will indeed be in the visible range of the light spectrum. The measurement body 16 in this case is transparent for both, the excitation light beam 18 as well as the detection light beam 22. In addition, a camera 32 or another imaging device is provided that allows for taking images of the contact surface 14 of the optical medium 16 in the direction from the inside of the measurement 16 body to the finger 12, to thereby record a fingerprint of the finger 12 resting on the contact surface 14. This fingerprint can be processed by a control unit 34 such as to identify a user via his or her fingerprint. The control unit 34 also serves for controlling the light sources 26 and 28 for the excitation light and the detection light, respectively, as well as the sensor 30. The control unit 34 is also in wireless connection with an external data processing device 36 to exchange data. For example, via the wireless connection, user-specific calibration data can be retrieved by the control unit 34 for the user that is identified via the fingerprint. The control unit 34 and the external data processing device 36 together form an example of a "control system" as referred to herein. The control system can be comprised by one or more processors, microcontrollers, computers, ASICs, FPGAs, or the like. The control system may be distributed, as indicated in FIG. 3, with various components in data communication with each other, or could be formed by a single control unit, such as the control unit 34, which would be devised for all of the control functionalities described herein. The control system may be generally embodied in hardware, in software, or a combination of both.

As is further seen in FIG. 3, the excitation and detection light sources 26 and 28, as well as the position sensitive detector 30 are all attached to a common carrier structure 38. This means that these components can be preassembled with precision on this structure 38, such that they do not need to be individually adjusted or calibrated when assembling the apparatus 10. One or more of the excitation and/or detection light sources 26 and 28, as well as the position sensitive detector 30 may also be directly mounted on the measurement body 16 in order to avoid additional adjustment or calibration.

In addition, the apparatus 10 comprises a corneometric device 40 that allows for measuring the water content of the skin. Corneometric devices for measuring the water content in the upper layer of the skin are per se known in the art and need not be described in detail here. For example, known corneometric devices measure the impedance, in particular capacitive impedance of the skin using two interdigital electrodes to which an AC voltage is applied. The corneometric device 40 of FIG. 3 is in contact with the fingertip 12 when the latter rests on the contact surface 14 of the measurement body 16.

The apparatus also comprises a pH-sensor 42 for measuring the pH value of the skin. pH sensors for measuring the pH value on surfaces, including those of the skin are per se known from prior art and need not be described in detail herein. pH sensors for measuring the pH value of the skin are commercially available for medical but also for cosmetic purposes.

Figure 4:
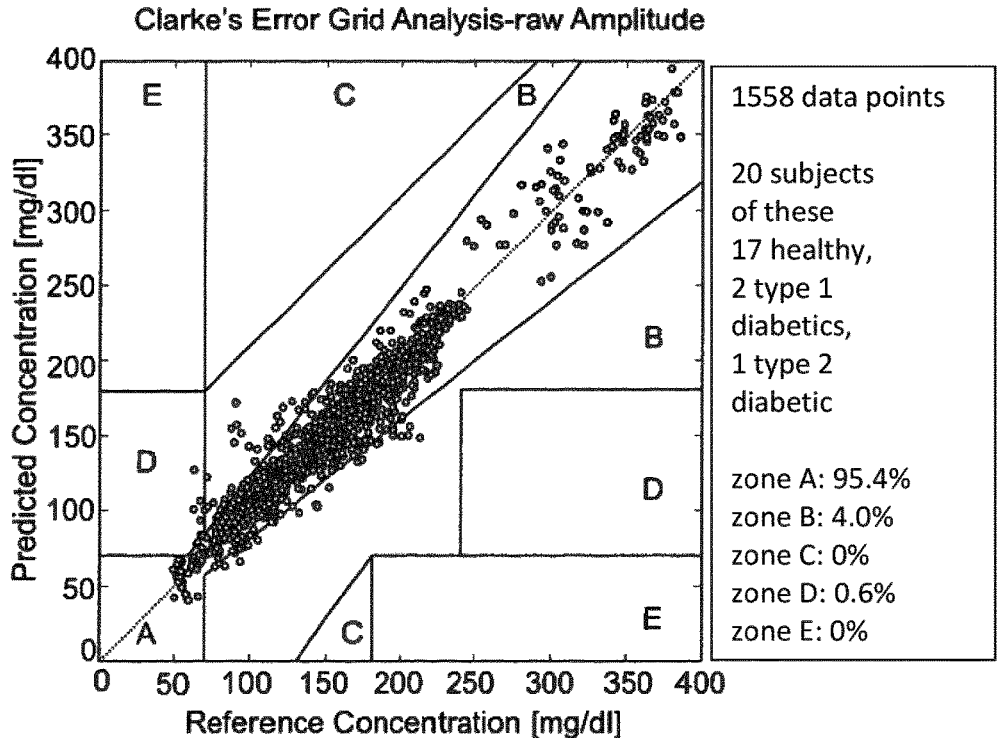
FIG. 4 shows results of a Clarke's error grid analysis obtained with an apparatus of the type shown in FIG. 3.

FIG. 4 shows results of a Clarke's error grid analysis obtained with an apparatus of the type shown in FIG. 3, illustrating that with the measurement procedure described with reference to FIG. 1 to 3, indeed very reliable blood sugar concentrations can be measured in a purely non-invasive manner. The data shown in FIG. 4 are taken from WO 2017/09782 A1 and do not yet reflect improvements of the present invention. The present invention allows for improving the reliability of the method even further, as will be described below.

Figure 5:
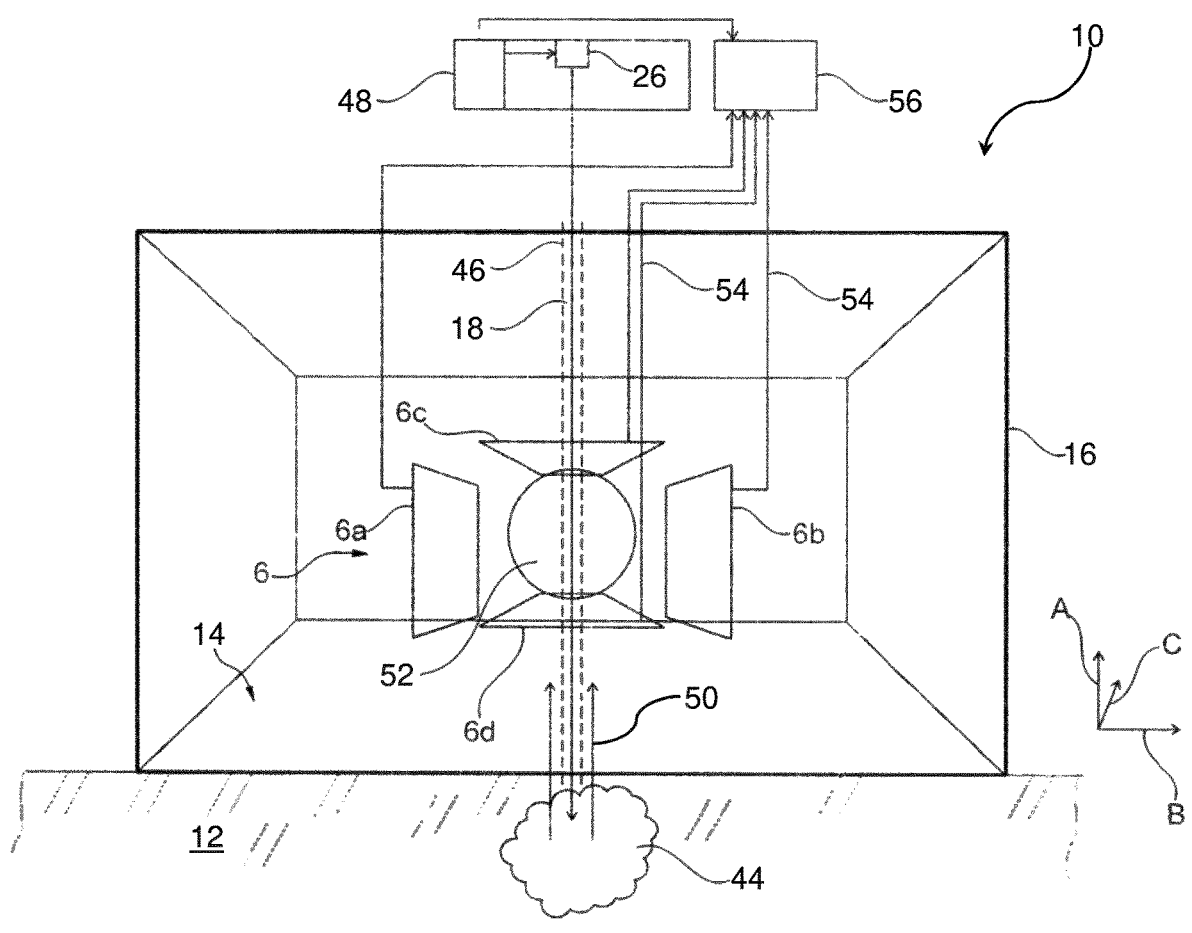
FIG. 5 is a schematic view of an apparatus for analyzing a material relying on response signals based on piezoelectric response to heat or pressure waves received by the material subjected to the analysis.

FIG. 5 schematically shows an apparatus 10 which relies on the same general principle involving absorption of heat pulses received by the measurement body 16 from the material 12 as that of FIGS. 1 and 3, but differs in the physical response exploited and the way the corresponding response signals are generated. Such an apparatus 10, as well as a large number of variations thereof are described in detail in WO 2019/11059782 incorporated herein by reference, such that a detailed description may be omitted herein. As before, the apparatus comprises a measurement body 16 having a contact surface 14 which is brought in contact or coupling with the skin of a finger 12. Also, a source 26 for an excitation light beam 18 with modulated intensity is provided, which is irradiated into a region 44 underneath the surface of the skin 12 and absorbed therein. In this embodiment, the excitation light beam 18 runs through a bore 46 in the measurement body 16 indicated by hashed lines through the measurement body 16, such that the material of the measurement body 16 itself need not be transparent for it.

A control unit 48 is provided for modulating the intensity of the excitation light beam 18. This can generally be done in various ways, including a mechanical chopper or an element having a transmissivity or reflectivity that can be electronically controlled. However, in preferred embodiments, the intensity is modulated by modulating the on/off times of the excitation light source 26 as well as the operating current during the on-times thereof.

A thermal wave caused by the time varying absorption of the intensity modulated excitation beam 18 in the region 44 of the skin 12, which is symbolically represented by arrows 50, enters the measuring body 16 where it can be detected in a detection region 52 which has piezoelectric properties. Pressure changes associated with received heat 50 or pressure waves lead to electrical signals in the form of voltage changes that can be recorded with electrodes 6a to 6d, which are connected via conducting leads 54 with an evaluation device 56 for analyzing the material (the skin of finger 12), which may be a digital processing device, for example a microcontroller or processor or a computer. In this case, the change in pressure resembles the physical response of the measurement body 16, or other component included therein, to heat received from the material 12 upon absorption of the excitation radiation, which is detected using the piezoelectric properties of the measurement body 16 or parts of it or piezoelectric elements embedded into the measurement body and the electrodes 6a to 6d, and which leads to electrical signals representing the response signal that is indicative of the degree of absorption of excitation radiation 18.

Figure 6:
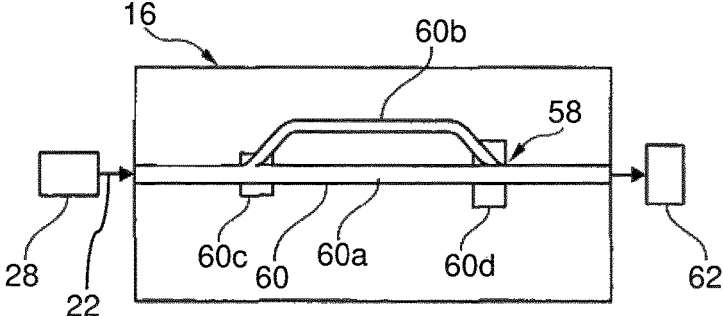
FIG. 6 is a schematic view of an apparatus for analyzing a material relying on response signals based on interferometrically detected phase changes in a detection light beam.

In alternative variants suggested by the present applicant, as for example disclosed in international application PCT/EP2019/064356 included herein by reference, the detection device may comprise an interferometric device which may be embedded into the measurement body and which is allowing for assessing said change in phase of a first part of the detection beam with respect to a second part of the detected beam, wherein only one of the parts of the detection beam passing through a measurement arm is affected by the effects of the heat or pressure wave in the measurement body, and generates on the output side of the interferometric device a response signal indicative of said change in phase in the measurement arm. In this case, the physical response of the measurement body 16 (or a component included therein) to heat received from said material 12 upon absorption of said excitation radiation 18 is again a local change in index of refraction, while the response signal is in this case an interferometric signal reflecting a change in the phase of one part of the detection beam due to the local change in refractive index. This is schematically illustrated in FIG. 6, where a measurement body 16 is shown which is to be brought in contact with the material (such as a finger, not shown in FIG. 6). In this case, the measurement body 16 may be a silicon substrate in which a light guiding structure 58 is provided, which forms an interferometric device 60. The interferometric device 60 forms a Mach-Zehnder interferometer, having a measurement arm 60a and a reference arm 60b. Detection light 22 generated by a detection light source 28 is fed into the light guiding structure 58 and is splitted by a splitter 60c into a portion or a part of the detection beam travelling along the measurement arm 60a and a portion or part travelling along the reference arm 60b, which portions are then united by a combiner 60d. The measurement body 16 is used or arranged such that the reference arm 60a is exposed to heat received from the skin upon absorption of excitation light, but not, or at least to a much lesser extent, the reference arm 60b. Due to received heat, the refractive index in the measurement arm 60a will change, which in turn leads to a phase shift of the detection light 22 travelling along the measurement arm 60a. Since the light travelling along the reference arm 60b is unaffected by the heat received, there will be a change in relative phase of the two portions of light combined by the combiner 60d, which leads to an interference pattern that can be detected using a detector 62 It should be noted that a camera as shown in FIG. 3 for detecting and analyzing a fingerprint may as well be combined with measurement bodies 16 and apparatus as shown in FIGS. 5 and 6.

Figure 7:
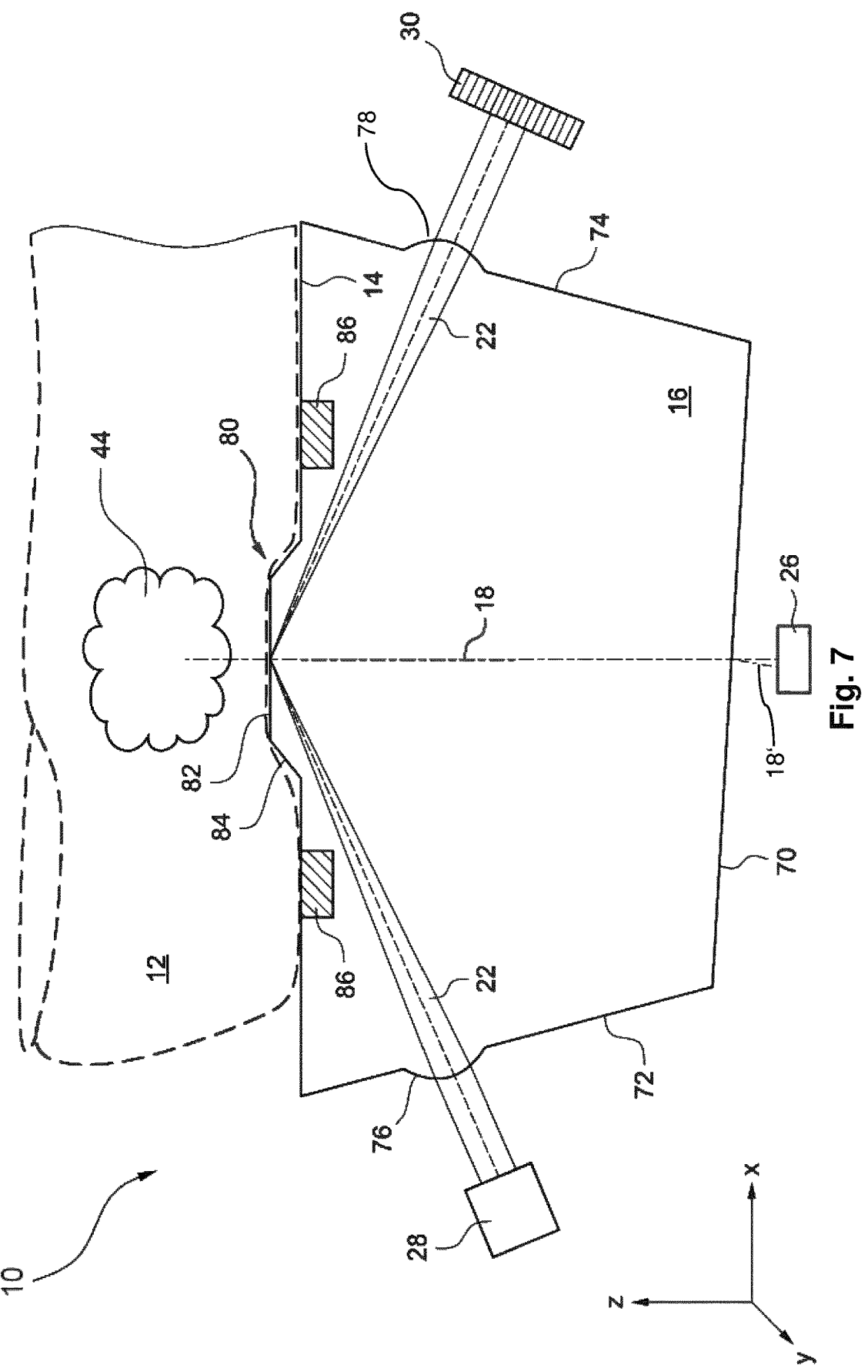
FIG. 7 is a schematic illustration of an apparatus according to one embodiment of the invention in a sectional side view.
Figure 8:
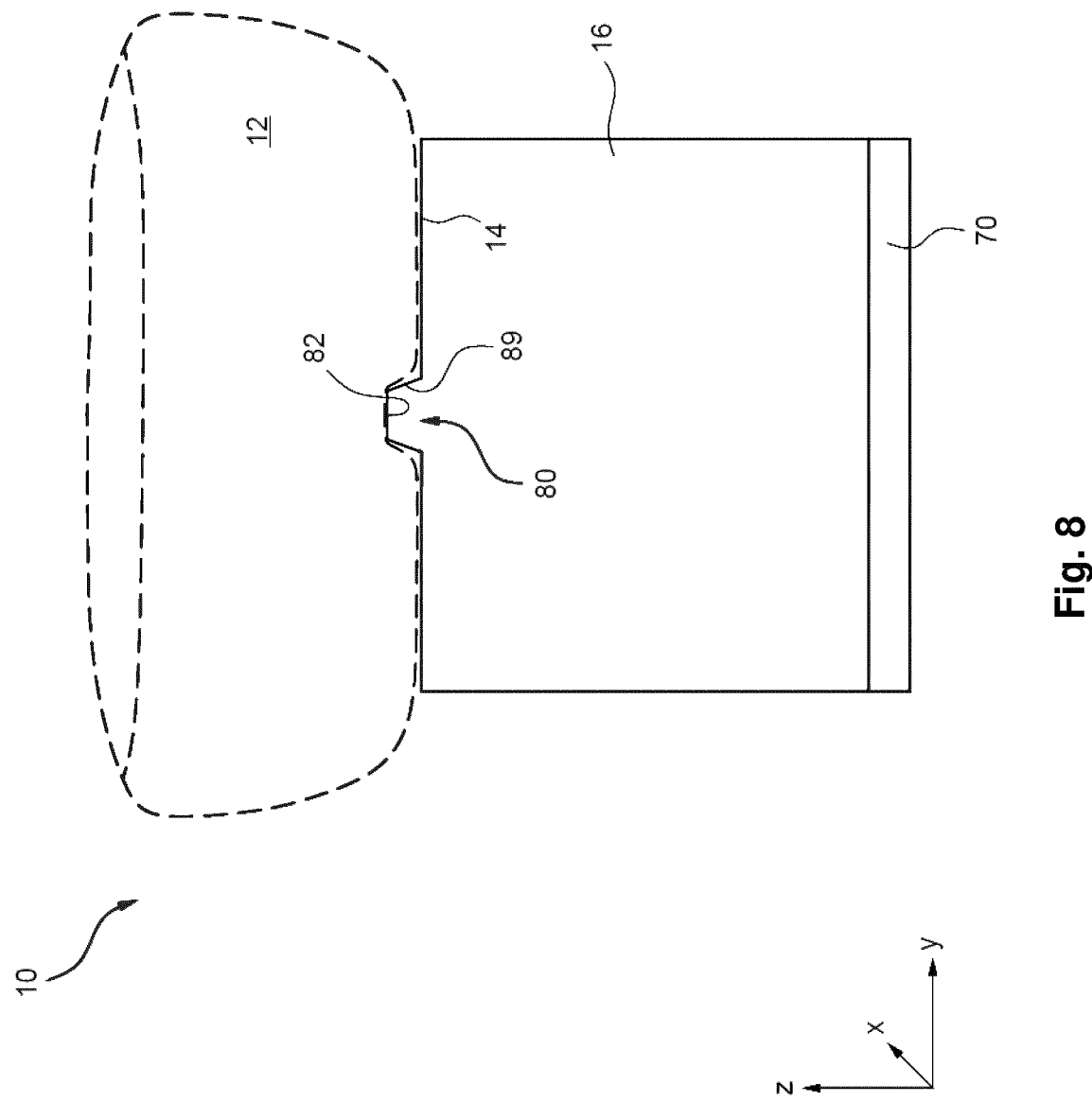
FIG. 8 is a schematic illustration of the apparatus of FIG. 7 in a sectional front view.

FIG. 7 shows a schematic illustration of an apparatus 10 according to an embodiment of the present invention in a side sectional view. FIG. 8 shows the same apparatus 10 in a front sectional view. In the embodiment shown in FIGS. 7 and 8, the material is again the skin of a finger 12 of a user, and the analyte to be assessed is glucose content in the skin, and in particular, in the interstitial fluid therein. The embodiment of FIGS. 7 and 8 allows for ensuring a reliable and consistent transmission of excitation radiation 18 into the skin of the finger 12. The measurement body 16 shown in FIGS. 7 and 8 is transparent for excitation radiation 18, and has, in addition to the contact surface 14, an entrance surface 70 for the excitation radiation 18, which is the bottom surface in the illustration of FIGS. 7 and 8.

The measurement body 16 further has an entrance surface 72 for the detection light beam 22, which in the illustration of FIG. 7 corresponds to the left side wall, and an exit surface 74 corresponding to the right side wall. Integrally with the entrance surface 72 and exit surface 74, a corresponding focusing lens 76 and collimating lens 78, respectively, are formed. In the shown embodiment, the focusing and collimating lenses 76 and 78 are formed monolithically with the remainder of the measurement body 16. In other embodiments, the focusing and collimation lenses 76 and 78 could be formed separately from the measurement body 16, but could be attached to the entrance and exit surfaces 70, 74, respectively, such that no individual adjustment thereof is necessary.

Moreover, on the contact surface 14 of the measurement body 16, a protrusion 80 is formed. The protrusion 80 has a front surface 82 that is in contact with the skin of the finger 12, and through which the excitation radiation 18, which in the present embodiment is formed by an excitation light beam 18 in the mid-IR range, is radiated into the skin. The protrusion 80 has four side walls 84, which are each tapering towards the front surface 82. This way, the area of the front surface 82 is smaller than the footprint area of the protrusion 80 on said contact surface 14. As is seen from the comparison of FIGS. 7 and 8, the protrusion 80 is ridge shaped, having a longer extension in a first direction which is the x-direction lying in the paper plane of FIG. 7, and a short extension in a second direction orthogonal to the first direction, which is the y-direction lying in the paper plane of FIG. 8.

Finally, on the contact surface 14, pressure sensors 86 are disposed, which measure the contact pressure between the finger 12 and the contact surface 14. The pressure sensors 86 are connected with a control system, such as the control unit 34 of FIG. 3 (not shown).

Next, the function of the various features shown in FIGS. 7 and 8 will be explained. As is seen in FIG. 7, the entrance surface 70 for the excitation radiation 18 is not parallel to the contact surface 14 or the front surface 82 of the protrusion 80. Instead, the measurement body is slightly wedge-shaped. Moreover, the excitation light source 26 is arranged such that the excitation beam 18 impinges on the entrance surface at an angle that deviates from 90°.

This is different from the arrangement shown for example in FIG. 3, where the excitation beam is deliberately caused to impinge onto the entrance surface at an angle of 90°, such as to avoid refraction and excess reflection of the excitation radiation beam at the entrance surface. However, as was explained above, with such an arrangement, part of the excitation radiation 18 will be reflected from the entrance surface 70 and may interfere with the excitation radiation 18 emitted from the excitation radiation source 26. The inventors found that this interference can lead to fluctuations in the intensity of excitation radiation 18 in the skin of the finger 12, thereby leading to artificial variations in the response signals that are completely unrelated to the analyte concentration. However, when avoiding perpendicular incidence of the excitation beam 18 on the entrance surface 70, interference between the incoming radiation 18 and the reflected radiation 18' shown in FIG. 7 can be suppressed, and the accuracy and reliability of the measurement as a whole can be improved.

In preferred embodiments, the angle of incidence should deviate from 90° only by a few degrees, if at all. Favorable angles of incidence could be 89.0° or less, preferably 88.0° or less, and more preferably 87.5° or less. The optimum choice for the angle will also depend on the distance between the excitation radiation source 26 and the entrance surface 70. The deviation from 90° should not be chosen larger than necessary for reliably avoiding the undesired interference effects. In preferred embodiments, the angle of incidence is therefore 82.0° or more, preferably 84.0° or more, and most preferably 85.0° or more.

The protrusion 80 has the special technical effect that the local contact pressure between the finger 12 and the measurement body 16 is increased. More precisely, the increased contact pressure occurs at the front surface 82 of the protrusion 80, which is where the excitation light beam 18 is coupled from the measurement body 16 into the skin of the finger 12. This increased contact pressure allows for ensuring a good and reliable optical coupling between the measurement body 14 and the skin.

The significant improvement obtainable with this protrusion 80 came as a surprise to the inventors, because in general, sufficient optical coupling was obtained in previous apparatuses of the applicant having an entirely flat contact surface 14, such that it was not apparent that the additional manufacturing costs and increased complexity involved with providing the protrusion 80 would be worth the effort.

However, the inventors found out that although the optical coupling with an entirely flat contact surface 14 generally appears satisfactory, particularly inconsistent or unstable optical coupling could be a source of inaccuracy of the measurement. As was explained in the summary above, the inventors noticed that the optical coupling may change during the course of a single measurement, i.e. without intentionally moving the fingertip on or even off the contact surface. This was found in some cases to cause a variation of the intensity of the excitation radiation actually absorbed by the analyte, and hence to a change in the response signal which was unrelated to the absorptivity of the analyte at the excitation radiation wavelength or the analyte concentration. In other words, loss of optical coupling during part of the measurement could be misinterpreted as reduced absorptivity at the given excitation wavelength. As was also explained above, assessing the analyte spectrum typically involves measuring the absorption at a plurality of characteristic wavelengths, for example wavelengths corresponding to peaks or local absorption minima of the analyte absorption spectrum, and further involves mathematical combinations of response signals associated with different wavelengths. For example, a response signal obtained at a local minimum of the absorption spectrum may be subtracted from that of an absorption peak to give a value representing the concentration of the glucose in the skin. Clearly, any variation in the optical coupling and hence the effective intensity of the excitation radiation in the material between measurements at different wavelengths, or even during a measurement at a certain wavelength, may lead to artefacts or inaccuracies in the measurement results.

As was explained in the summary of the invention, it is not entirely clear precisely why the optical coupling between the contact surface and the material should change during the measurement, e.g. whether it is because the user fails to keep the contact pressure between the finger and the contact surface constant, or whether the user inadvertently moves the fingertip on the contact surface. Irrespective of the precise underlying reasons, the inventors noticed that the optical contact can be significantly stabilized using a protrusion such as the protrusion 80 as shown in FIGS. 7 and 8, having front surface 82 in contact with the skin of the finger 12 with a local increased contact pressure. The front surface may have a size of less than 5 mm$^2$, in particular less than 3 mm$^2$ and may be flat or curved in a concave or convex manner.

To further ensure constant contact pressure during the measurement, pressure sensors 86 are provided. The pressure sensors 86 generate signals indicating the contact pressure between the finger 12 and the contact surface 14 of the measurement body 16. The signals are conveyed to a control system (not shown) which is configured to check whether the sensed contact pressure is below a predetermined threshold value. If this is found to be the case, this is indicated to the user by means of a suitable output device, such as a display, a light signal, an acoustic signal or the like, such that the user can be prompted to increase the contact pressure. Moreover, the control system is configured to prevent an analyte measurement process from starting while the contact pressure is below the threshold, thereby avoiding measurements to be carried out that have doubtful quality and possibly have to be repeated, which can lead to impatience or frustration of the user. Moreover, if during the measurement it is found that the contact pressure falls below the threshold, the analyte measurement process is interrupted, again giving the user the opportunity to resume the original contact pressure, such that the measurement can be completed. A pressure sensor could also be located underneath the protrusion 80 in the measurement body 16 and be implemented as a piezoelectric element (not shown) which may be transparent for the excitation beam.

Note that each of the features and functionalities explained so far with reference to FIG. 7 are related with reliably coupling a consistent amount of excitation radiation into the skin of the finger 12, and are as such independent of the specific type of physical response of the measurement body (or a component included therein) to heat or pressure waves received from the skin of finger 12 or of the detection device generating corresponding response signals. Accordingly, these features can be used in combination with any of the variants shown in FIGS. 1, 3, 5 and 6.

In the embodiment of FIG. 7, the physical response to heat or pressure waves received by the measurement body 16 is a local change in refractive index, and this physical response is detected via a deflection of a detection light beam 22 that is reflected at the front surface 82 of the protrusion 84. As is seen in FIG. 7, the detection light beam 22 is generated by a detection light source 28, and the deflection of the detection light beam 22 is detected using a position sensitive detector (PSD) 30, which may also be referred to as a position sensitive device. As understood herein, the "deflection of the detection light beam 22" denotes the total deviation of the detection light beam at the corresponding detection device, and with specific reference to the embodiment of FIG. 7, it denotes the shift of the position of the detection light beam 22 on the PSD 30. This deviation is the combined effect of all changes to the propagation of the detection light beam 22 along its light path that are caused by the local change in refractive index.

The specific ridge-shaped geometry of the protrusion 80 shown in FIGS. 7 and 8 has been adapted to this detection setup. The detection light beam 22 prior to and after reflection at the front surface 82 of the protrusion 80 define a detection light plane, which in the embodiment of FIGS. 7 and 8 corresponds with the x-z-plane, i.e. the paper plane of FIG. 7, and this detection light plane coincides with the first, longer direction of the ridge-shaped protrusion 80. Indeed, as is apparent from FIG. 7, this larger extension of the protrusion 80 in the detection light plane is necessary such that the incoming and reflected detection light beams 22 fit into the protrusion 80. Conversely, as is apparent from FIG. 8, in a direction perpendicular to this detection light plane, i.e. the "second direction" of the ridge-shaped protrusion 80, the extension can be made much smaller, to thereby keep the surface area of the front surface 82 as a whole small and hence increase the local contact pressure.

Moreover, the focusing lens 76 at the entrance surface 72 of the detection light beam 22 allows for keeping the detection light beam diameter 22 narrow in the region where it is reflected on the front surface 82 of the protrusion 80, which is also the region where the thermal lens (not shown in FIG. 7) will be formed. A narrow beam diameter promotes a clear and characteristic deflection of the detection light beam 22 at the thermal lens, which itself is only of comparatively small size.

The collimating lens 78 at the exit surface 74 of the detection beam 22 allows for keeping the diameter of the detection beam 22 at least nearly constant on its travel between the exit surface 74 and the PSD 30. This allows for increasing the distance between the PSD 30 and the exit surface 74, which means that any deflection angle acquired by the detection beam 20 will lead to a larger shift of the position where the detection beam 22 impinges on the PSD 30, thereby increasing the signal-to-noise ratio of the response signal. For example, the distance between the site of reflection at the front surface 82 of the protrusion 80 and the PSD 30 may be 4 cm or more, in some embodiments even 9 cm or more.

In the embodiment shown in FIG. 7, both, the focusing lens 76 and the collimating lens 78 are shown as spherical lenses which have focusing and collimating effect in both principal directions. However, in other embodiments, especially the collimating lens 78 could be a cylinder lens, which has its collimating effect only in the y-direction in FIG. 7, while different from what is shown in FIG. 7, the detection light beam 20 could spread out in the x-z-plane, i.e. the paper plane of FIG. 7. This means that the light spot of the detection light beam 22 on the PSD 30 will be oblong, with the longer diameter being parallel to the sensing direction of the PSD 30, which is also the direction in which the light spot will move upon deflection of the detection light beam 20. This elongate shape of the light spot has found to likewise lead to a better signal-to-noise ratio and a better linearity of the response signal.

As understood herein, the "deflection" of the detection light beam 20 relates to the total deviation of the detection had been 20 from its "undisturbed" light path, i.e. without the local change in refractive index due to heat or pressure waves received by the measurement body 16, as measured by the detection device, such as the PSD 30. This "deflection" is hence the accumulated effect that the local change of refractive index has on the detection light beam 20 along its light path. In practice, the deflections will always tend to be small, and in order to get more accurate and reliable measurement results, it is important to raise the signal-to-noise ratio of the response signal. One possible approach has been explained above with reference to FIG. 7, namely by increasing the distance between the exit surface 74 and the PSD 30. Further ways to improve the signal-to-noise ratio will be discussed with reference to FIG. 9 to 11 below.

Figure 9:
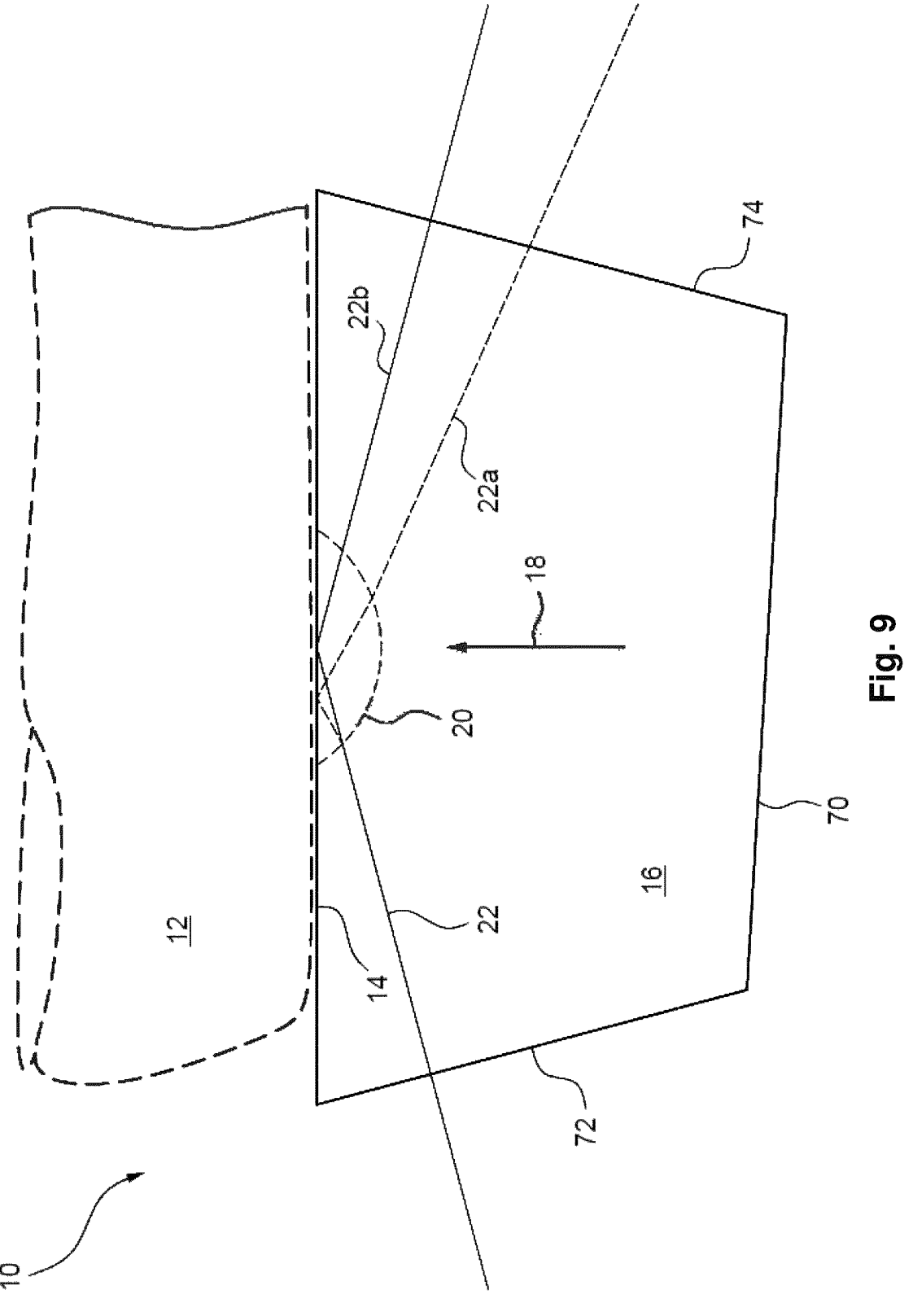
FIG. 9 is a schematic illustration of an apparatus illustrating the deflection of a detection light beam.
Figure 10:
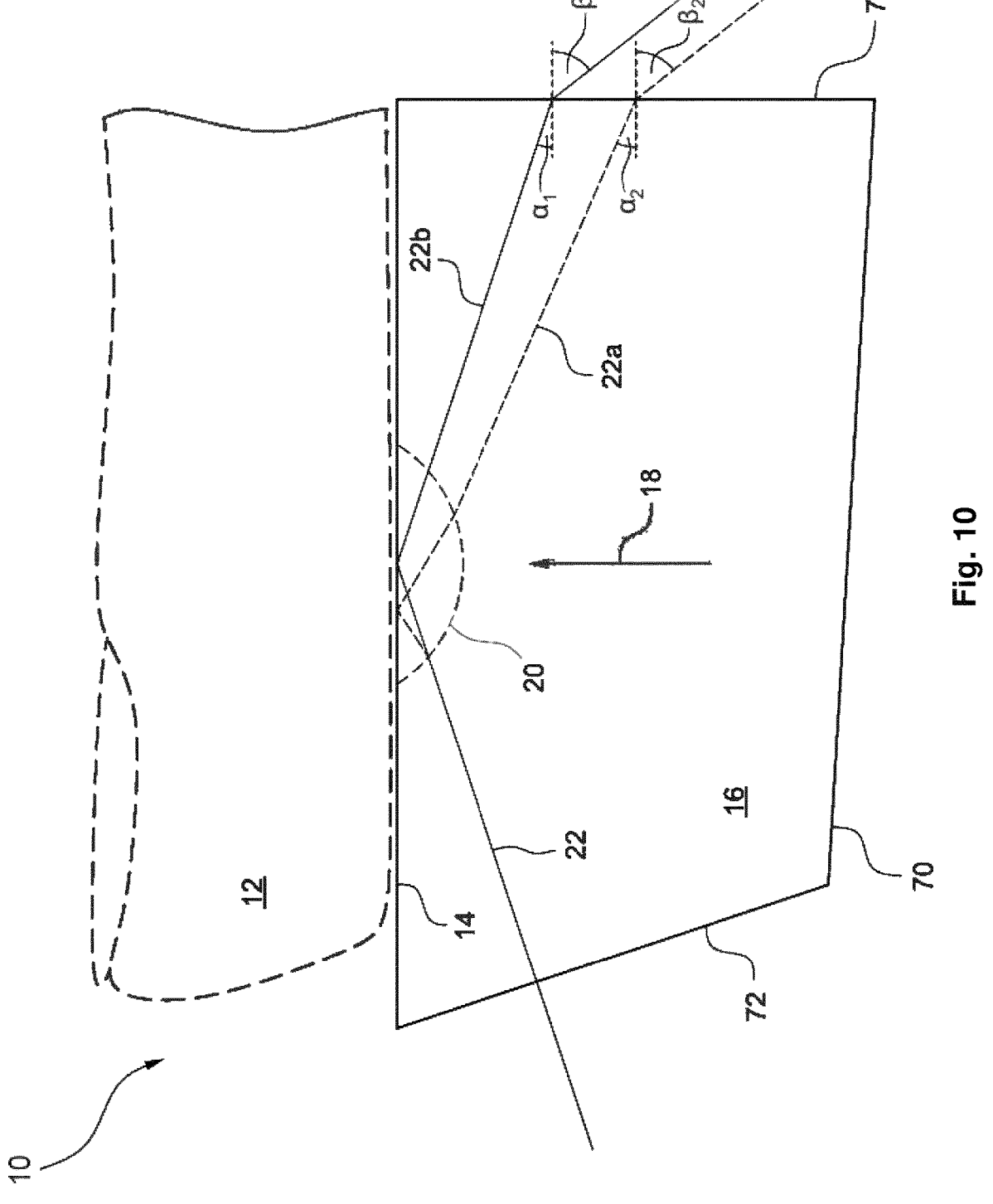
FIG. 10 is a schematic illustration of an apparatus similar to the one of FIG. 9, but with additional refraction of the detection light beam at the exit surface of the measurement body.

Without wishing to be bound by theory, FIG. 9 illustrates a mechanism of the deflection as currently understood by the inventors, that is fully consistent with the actual measurements. In FIG. 9, the unperturbed detection light beam is shown in solid line, with an incoming portion 22 and an outgoing portion 22*b*. When an excitation radiation pulse 18 is absorbed in the skin of FIG. 12, as explained above, a heat pulse is generated that travels through the skin and into the measurement body 16, where it causes a local change in refractive index, which is referred to as a "thermal lens" herein and schematically shown at reference sign 20 in FIG. 9. The thermal lens 20 is in this embodiment found to be a region of increased refractive index, which leads to the refraction as indicated by the dashed refracted and reflected detection light beam 20*a*. The deviation of the reflected detection light beam 22*a* from the unperturbed reflected detection light beam 22*b* is referred to as the "deflection" herein.

Note that in FIG. 9, the entrance and exit surfaces 72 and 74 of the measurement body 16 are angled such as to form a right angle with the incoming and outgoing detection light beam 22. This orthogonal arrangement of the optical boundary is the natural choice in the field, as it allows for reducing reflection and also for avoiding diffraction, which would make the optical setup more complicated. However, in the embodiment of FIG. 10, at least the exit surface 74 is arranged such as to not be perpendicular to the reflected detection light beam 22*b*. Instead, the detection light beam 22*b* forms an angle $\alpha_1$ with respect to the normal to the exit surface 74, such that the undisturbed detection light beam 22*b* is refracted when exiting the measurement body 16 with an angle $\beta_1$ that is larger than $\alpha_1$, since the refractive index of the measurement body 16 is higher than that of the surrounding, which in the present embodiment is air.

The deflected light beam 22*a* is likewise refracted at the exit surface 74. However, due to the interaction with the thermal lens 20, the angle of incidence $\alpha_2$ is larger than in the undisturbed detection beam 22*b*, and according to Snell's law, the angle of refraction $\beta_2$ is considerably bigger than $\beta_1$. In other words, the difference between the refracted angles, $\beta_2 - \beta_1$ is larger than the difference between the angles of incidence $\alpha_2 - \alpha_1$, i.e. $\beta_2 - \beta_1 > \alpha_2 - \alpha_1$, such that the deflection of the reflected detection light beam 22*a* as measured by the PSD 30 (not shown in FIG. 10) is increased. This allows for further increasing the signal-to-noise ratio.

Figure 11:
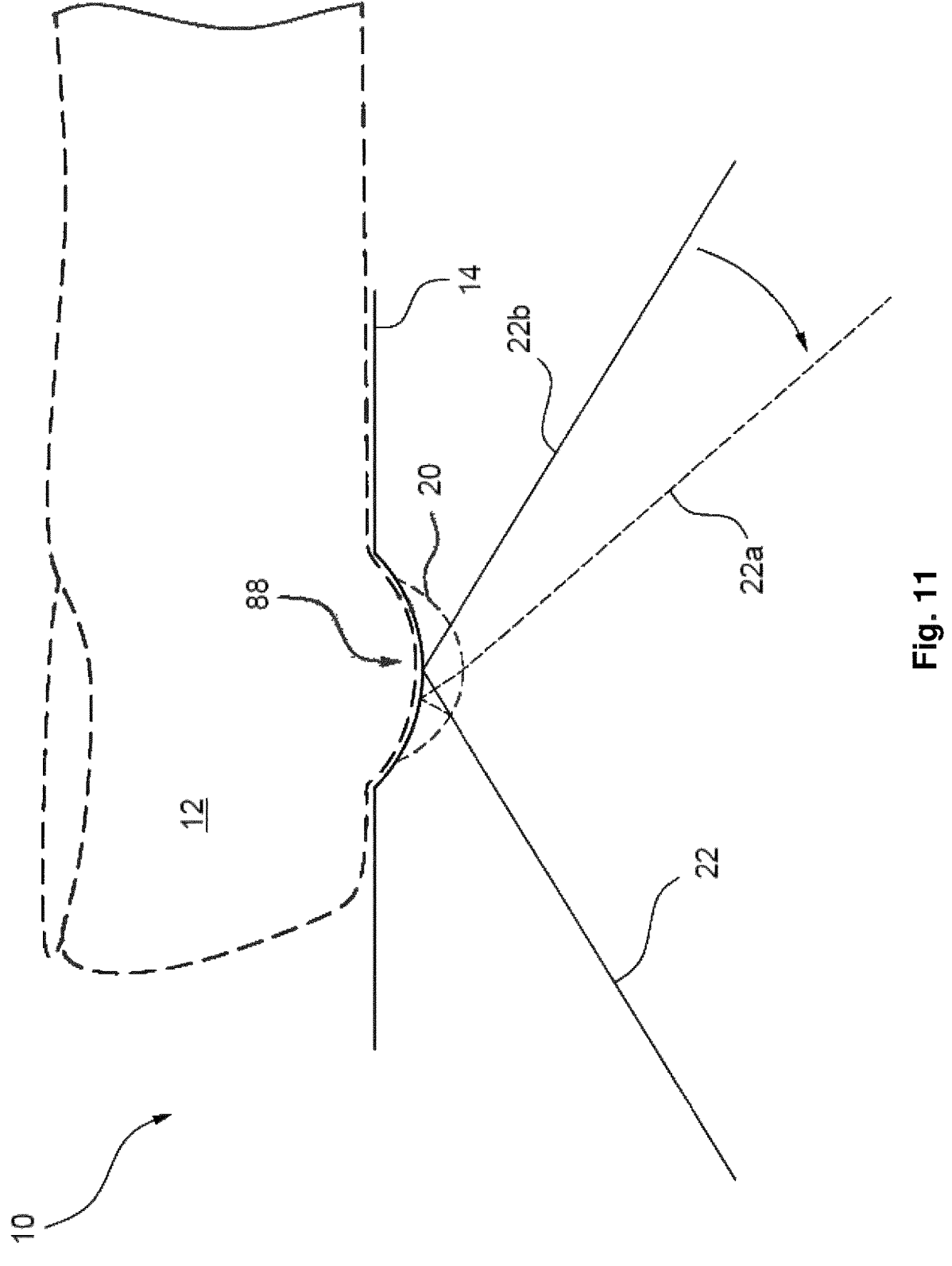
FIG. 11 is a schematic illustration illustrating an increased deflection using a curved reflection surface for the detection light beam.

Finally, with reference to FIG. 11, an embodiment is shown where the contact surface 14 of the measurement body 16 is curved in the region where the detection light beam 22 is reflected. In other words, the measurement body in this region has a concavely curved recess. As is schematically shown in FIG. 11, part of the deflection of the light beam 22 due to the local change in refractive index occurs before the detection light beam 22 is reflected at a surface of the measurement body that is in thermal or pressure-transmitting contact with the finger 12. This means that the local change in refractive index also leads to a shift of the location precisely where on the surface the detection light beam 22 will be reflected.

In view of this understanding, in the embodiment shown in FIG. 11, the contact surface 14 has a curved portion 88. Due to this curvature, a change in location precisely where the detection light beam 22 is reflected on the curved portion 88 is accompanied by a change of angle of incidence, and hence leads to a corresponding change in the angle of reflection as well, as can be seen in FIG. 11. Accordingly, using a curved reflection surface, the total deflection assessed by the detection device, such as the shift in position of the impinging detection light beam 22 detected with the position sensitive detector 30, can be increased, thereby further allowing for increasing the signal-to-noise ratio. Note that in FIG. 11, the curved portion 88 is shown to be formed in the otherwise flat contact surface 14, but a curved portion could likewise be formed in the front surface 82 of the protrusion 80 shown in FIG. 7 and FIG. 8. moreover, while in the embodiment shown in FIG. 11, the curved portion 88 was concave, similar effects can be obtained with convexcurved portions (not shown) as well, since in this case too, the local change in refractive index will be accompanied by a change in the position where the detection light beam impinges on the curved portion, and hence a change in angle of incidence.

Moreover, in FIG. 11, the curved portion 88 is shown to have a spherical shape i.e. having a same or similar curvature in two principal directions. However, in other embodiments the curved portion 88 could be curved predominantly or even exclusively only in one direction, for example having the shape of a section of a cylinder (with the section plane parallel to the cylinder axis). This is particularly advantageous in case of concave curved portions 88, where in this case the finger 12 could be placed parallel to the longitudinal axis of the concave curved portion, allowing for a particularly good contact on the curved surface of the curved portion. As was mentioned above, in preferred embodiments, the radius of curvature of the curved portion 88 in at least one principal direction is in the range of 5 to 30 mm, more preferably 10 to 20 mm. In preferred embodiments, the width of the curved region 88 in the principal direction is at least 300 μm, and at most two times the radius of curvature.

Figure 12:
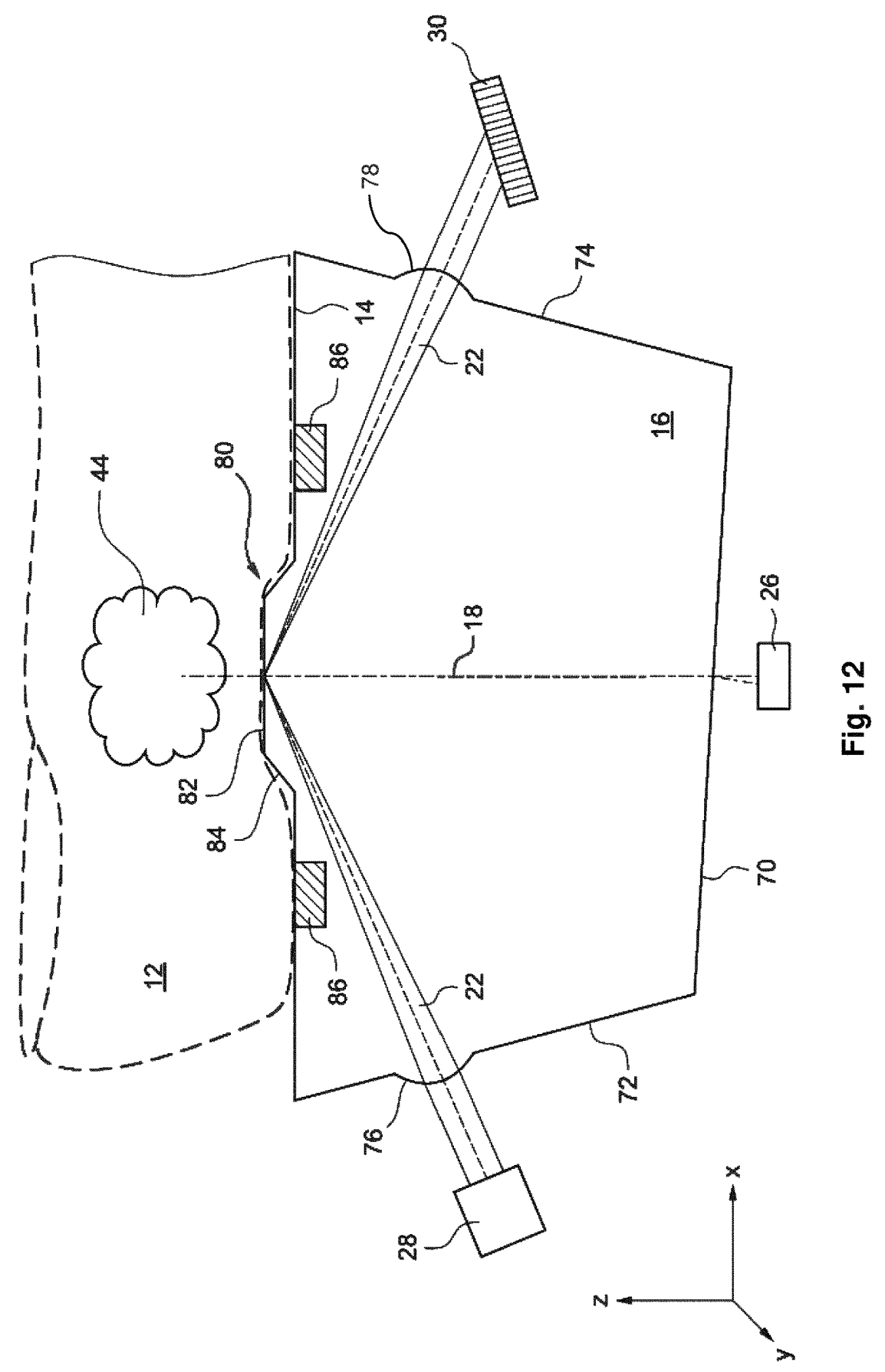
FIG. 12 is a schematic illustration of an apparatus similar to that of FIG. 7, in which the position sensitive detector is arranged at an angle with respect to the detection light beam.

As was mentioned above, in many embodiments it is advantageous if the light spot of the detection light beam 22 on the PSD 30 has an elongate shape, for example and elliptic shape with its long axis being parallel to the detection direction. This elongate shape can be obtained for example by collimating the detection light beam 22 only in a direction orthogonal to the detection direction, as was explained with reference to FIG. 7 above. However, in addition or alternatively, the elongate shape of the light spot can be obtained by tilting the PSD 30 in the detection light plane with respect to the detection light beam 22, as shown in FIG. 12, such that it impinges on the PSD 30 with an angle deviating from 90°. For example, the angle of incidence onto the detecting surface of the PSD 30 could be less than 80°, preferably less than 70°, and most preferably less than 50°.

Figure 13:
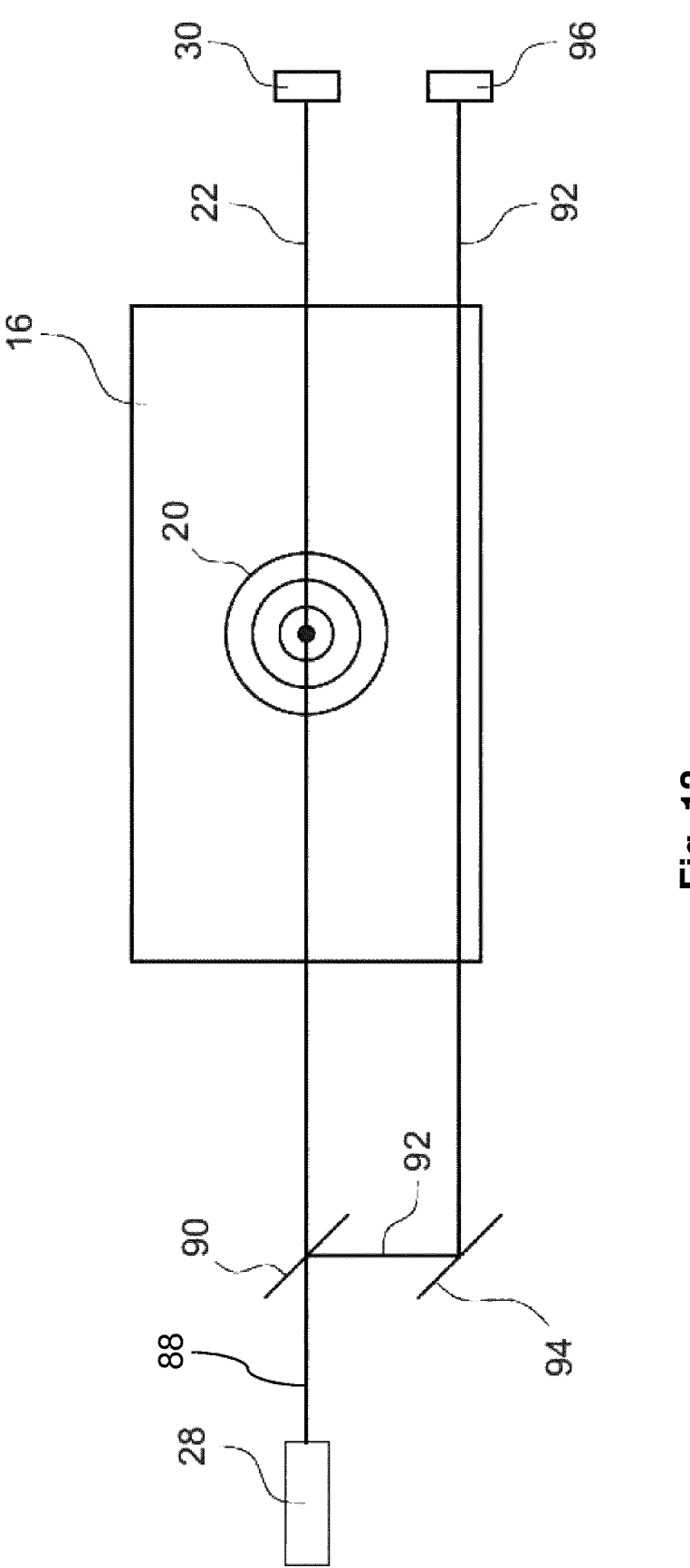
FIG. 13 is a schematic top view of an apparatus similar to that of FIG. 7, in which in which a reference light beam is used in addition to the detection light beam.
Figure 14:
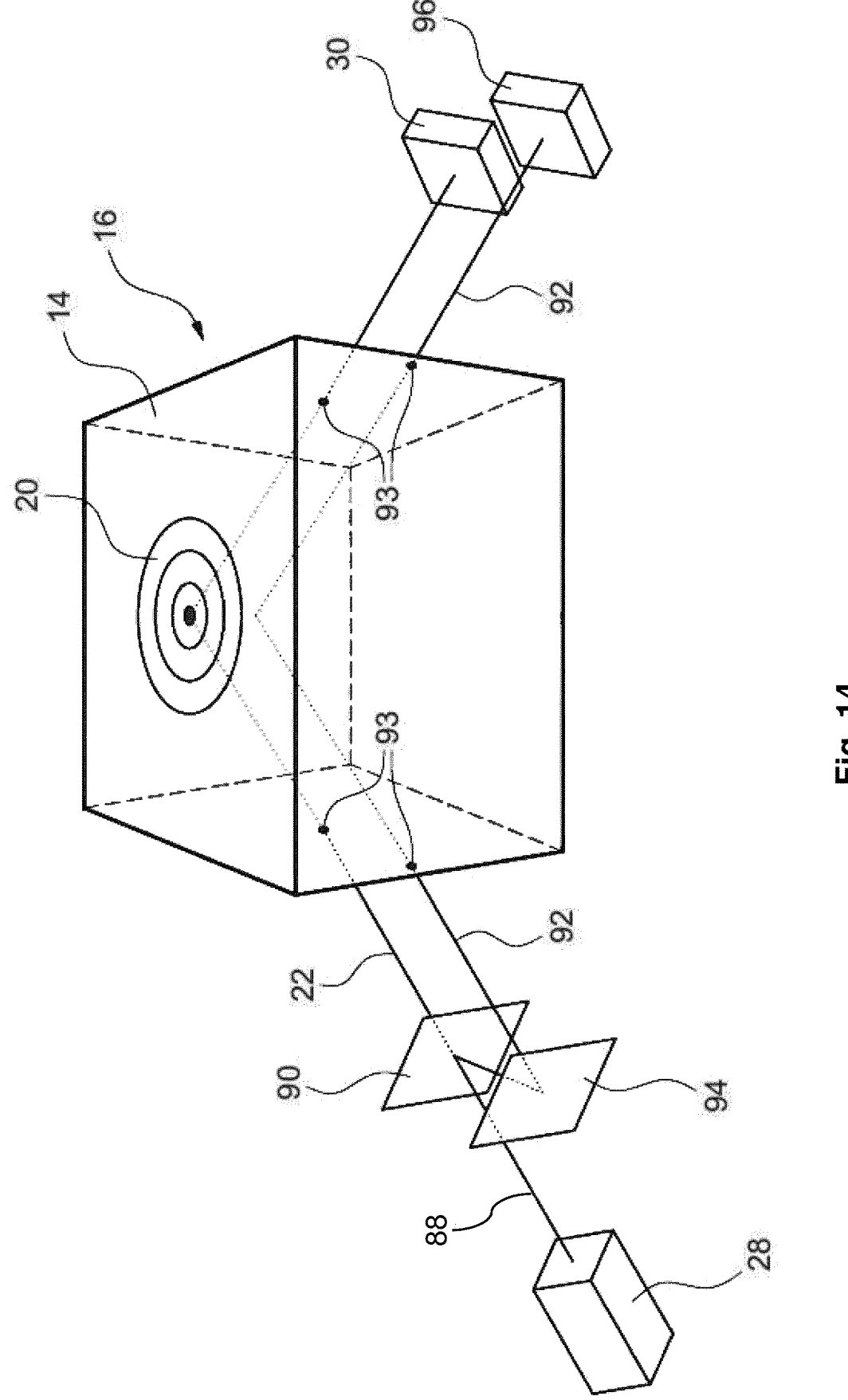
FIG. 14 is a perspective view of the apparatus of FIG. 13.

FIGS. 13 and 14 show a yet further apparatus 10 which is similar to that of FIG. 7, in a top view and in a perspective view, respectively. Similar to the apparatus of FIG. 7, the apparatus of FIGS. 13 and 14 comprises a detection light beam 22 which is reflected on a contact surface 14 of a measurement body 16, and a detection device, such as a PSD 30, that allows for detecting a deflection of the detection light beam 22 due to interaction with a thermal lens indicated at reference sign 20. In the embodiment of FIGS. 13 and 14, the detection light beam 22 is derived from a source light beam 88 by means of a splitter 90. The splitter 90 transmits a portion of the source light beam 88 which forms the detection light beam 22, and reflects another portion, which forms a reference light beam 92. Using a mirror 94, the reference light beam 92 is likewise directed to be totally or partially reflected at the surface 14 of the measurement body 16 at a location that is close to the reflection location of the detection light beam 22, and in particular also in a region where the finger 12 (not shown) in operation would contact the contact surface 14. However, the reflection point of the reference light beam 92 on the contact surface (or more precisely, at the interface between the contact surface 14 and the material, i.e. finger 12) is sufficiently far away from the area where the excitation beam 18 is absorbed, such that any effect of heat or pressure waves received from the finger 12 upon absorption of the excitation radiation 18 is negligible. This is illustrated in FIGS. 13 and 14, where it can be seen that the thermal lens 20 does not extend to the region where the reference light beam 92 is reflected on the contact surface 14 of the measurement body 16.

In FIG. 14, reference signs 93 indicate the points where the detection light beam 22 and the reference light beam 92 enter and leave the measurement body 16, and are mainly shown to assist in imagining the three-dimensional structure. Note that in the schematic illustration of FIG. 14, no refraction of the detection and reference light beams 22, 92 at the entrance and exit surfaces is shown for simplicity. A further detection device 96 is provided for detecting a degree of deflection of the reference light beam 92, and in the embodiment shown, it is formed by an identical type of PSD as the PSD 30.

It is seen that the reference light beam 92 will be exposed to all or almost all the same types of noise, vibrations, perturbations or external influences as the detection light beam 22, except for the effect of the thermal lens 20, or in other words, the heat or pressure wave received due to absorption of the excitation light beam 18. Accordingly, all or at least most types of external effects that could lead to a deflection of the detection light beam 22, other than those attributable to the absorption in the material, will also influence the reference light beam 92, and can be measured by the additional detector 96. Then, the measurement result of the additional detector 92 with respect to the reference light beam 92 can be used to correct for these effects in the measurement result of the PSD 30 with respect to the detection light beam 22, to thereby improve the measurement signal quality.

Figure 15:
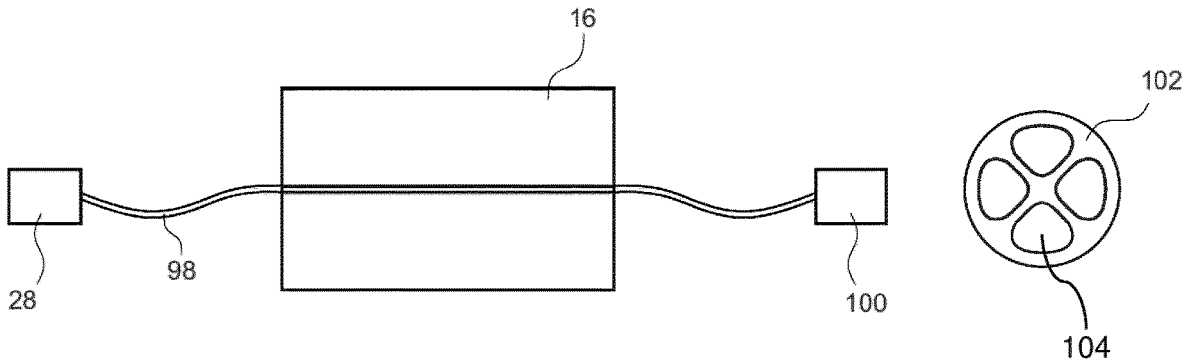
FIG. 15 is a schematic view of a further apparatus in which the response signal corresponds to a change in optical modes formed in a fiber contained in the measurement body.
Figure 16:
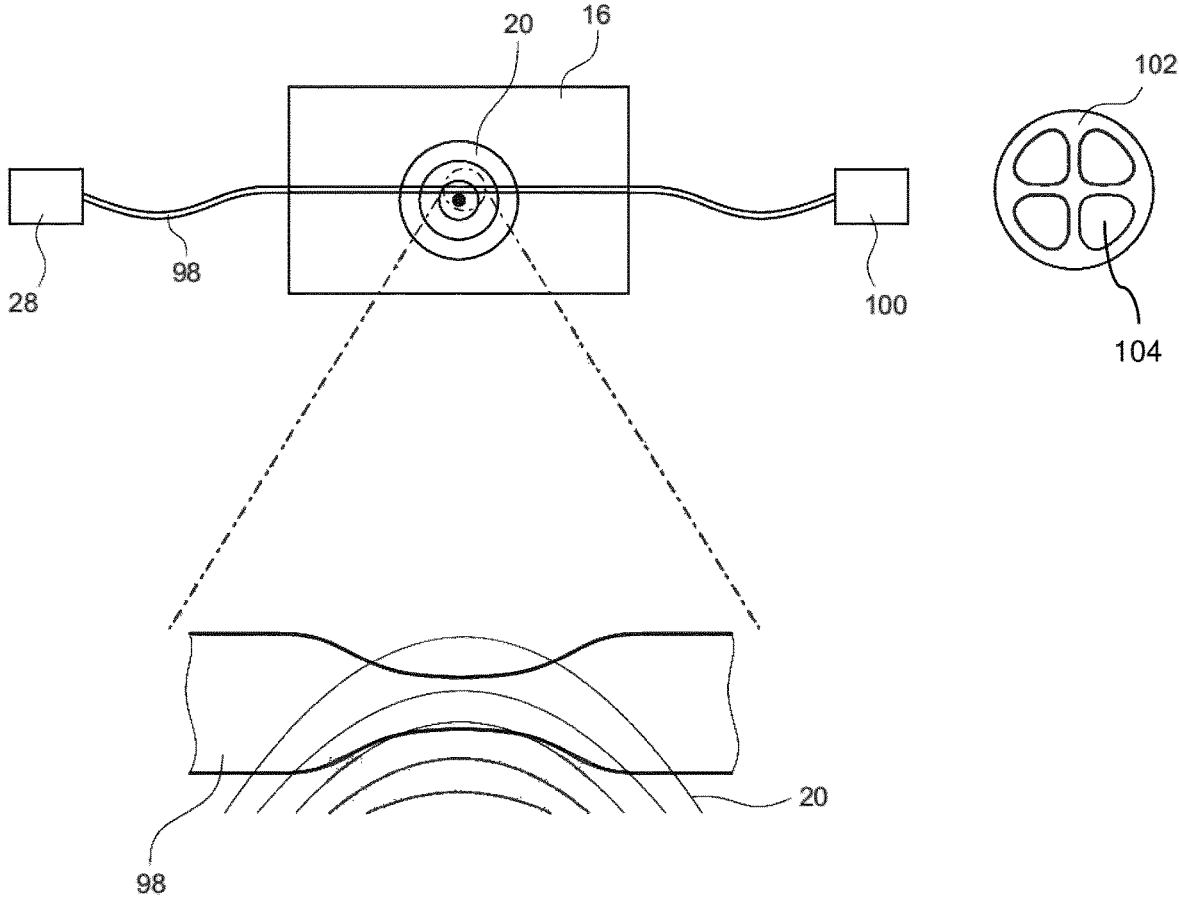
FIG. 16 shows the same apparatus as FIG. 15 in a situation where a thermal gradient is formed in the measurement body.

With reference to FIGS. 15 and 16, a further embodiment of an apparatus is shown, which comprises an optical fiber 98 embedded in a measurement body 16. A detection light source 28 is provided at one end of said fiber 98 for coupling detection light into said fiber 98. At the other end of the fiber 98, a mode detector 100 is provided. The mode detector 100 is suitable for detecting changes in optical modes of said detection light in response to the heat or pressure waves received by the measurement body 16 from said material. For example, the mode detector 100 could comprise a camera suitable for visualising the modes, and more precisely, an interference pattern of optical modes. On the right of FIG. 15, an image generated by such mode camera is schematically shown, in which optical modes 104, and more precisely, an interference pattern of optical modes, can be seen in a certain rotational orientation.

FIG. 16 shows the same apparatus as FIG. 15, in which however a thermal gradient 20 is formed due to heat or pressure waves received from the material, such as a finger 12 (not shown in FIGS. 15 and 16). This will lead to a transient deformation of the optical fiber 98 which is shown in the enlarged portion of FIG. 16, where the deformation is highly exaggerated for illustration purposes. Such a transient deformation of the optical fiber 98 will lead to a change in the optical modes as detected by the mode camera 100. In the exemplary embodiment illustrated in FIG. 16, the change in the modes amounts to a rotation of the interference pattern of the modes, as seen by comparison of the schematically shown mode images in FIG. 15 and FIG. 16. In other embodiments, the change in the modes could for example correspond to a shift of the interference pattern of the modes.

In the embodiment shown, the mode detector 100 comprises a processor (not individually shown) configured for detecting changes in the modes based on an image analysis of the camera images. As mentioned above, detectable changes in optical modes may comprise a shift or a rotation of an interference pattern of optical modes within the fiber and also on the mode camera 100. The distance of the shift or a rotation angle is hence a quantitative parameter that is associated with the amount of heat or intensity of a pressure wave received from the material, and hence ultimately indicative of the amount of excitation light absorbed by the material. The apparatus of FIGS. 15 and 16 is advantageous in that it is very simple robust and needs hardly any adjustment of optical components. It is particularly useful for portable apparatus.

Figure 17:
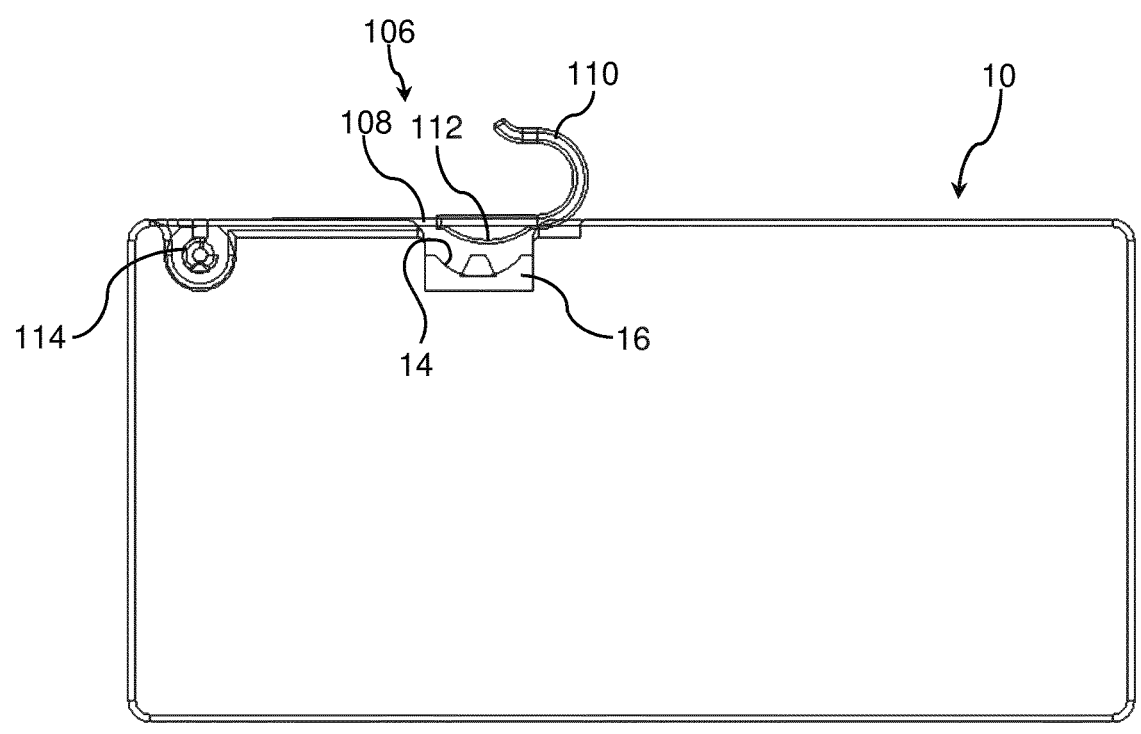
FIG. 17 shows an apparatus including a clamping device.
Figure 17:
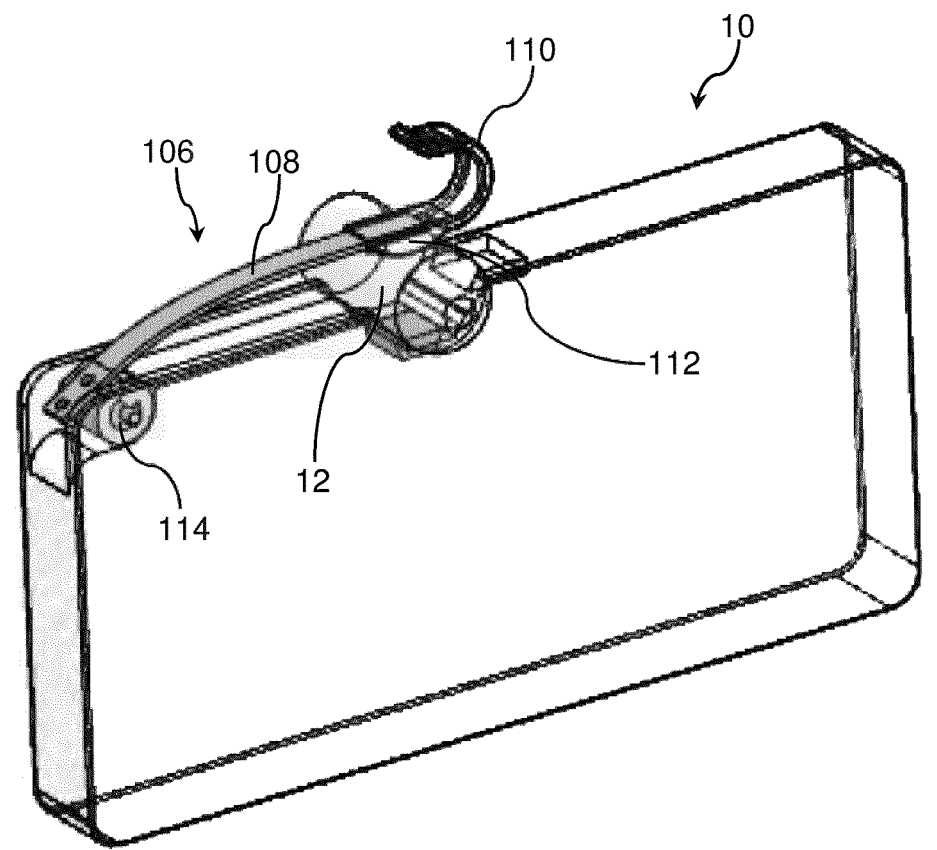

FIG. 17 shows a side view and perspective view of an apparatus 10 according to a further embodiment. The apparatus 10 is a portable glucose measuring device having a size similar to that of a small smart phone. In the upper view of FIG. 17, a measurement body 16 having a contact surface 14 is shown which in this case has a curved portion similar to that of FIG. 11. On the contact surface 14, a finger 12 can be placed in a manner shown in FIG. 17, where the finger 12 is only schematically represented by a cylindrical structure. While the further details of the apparatus are not shown in FIGS. 16 and 17, the measurement principle of the device is similar to that of FIG. 11, using a detection light beam (not shown) that is reflected on a curved surface. As was explained with reference to FIG. 11, this leads to particularly large deflections of the measurement beam and hence a particularly high signal-to-noise ratio.

Further shown in FIG. 17 is a clamping device 106, comprising a clamping member 108. The clamping member 108 is pivotably mounted at a first end (left end in the figure) and biased by a torsion spring 114 into a closed position shown in the upper view of FIG. 17, in which it is close to the contact surface 14. At the second end of the clamping member 108, a handle member 110 is provided allowing for gripping the clamping member 108 and rotating it against the biasing force of the torsion spring 114 into an open position in which the clamping member 108 is moved away from the contact surface 14 of the measurement body 16. The finger 12 can be placed on the contact surface 14 when the clamping member 108 is in the open position, and said clamping member 108 is suitable for pressing said finger 12 against the contact surface 14 due to the biasing force towards the closed position. This way, a predefined contact pressure can be ensured. Close to the second end of the clamping member 108, a cushion 112 is formed, which rests on the finger 12 when it is held by the clamping member 108 in a manner shown in FIG. 17. In the embodiment shown, a pressure sensor (not shown) is provided in the cushion 112, monitoring the contact pressure in a similar manner as the pressure sensors 86 shown in FIG. 7. Note that the clamping mechanism is not limited to use in a handheld device, but could also be provided e.g. on a tabletop device or any other variant. Moreover, the biasing force of the clamping member 108 need not be generated by a torsion spring such as the torsion spring 114, but could also be provided by the clamping member 108 acting as a leaf spring. Instead of the torsion spring 114, there could be an adjustable mount allowing for adjusting the rest position of the clamping member 108 (leaf spring) and hence the biasing force created thereby.

Figures 18, 19:
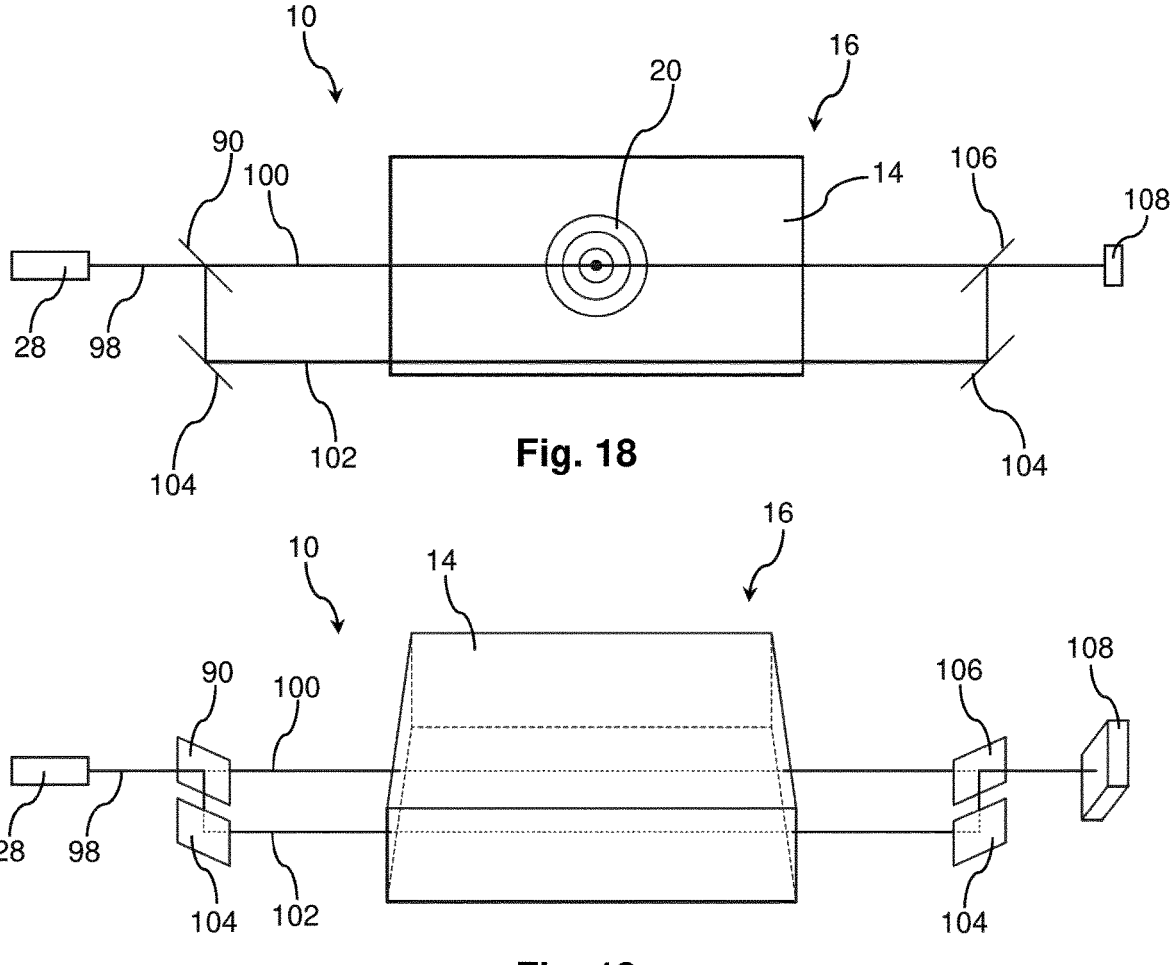
FIG. 18 is a top view of a further apparatus for measuring an analyte based on an interference signal of two portions of a detection light beam.
FIG. 19 is a perspective view of the apparatus of FIG. 18.

FIGS. 18 and 19 show a yet further apparatus 10 which is in some respects structurally similar to that of FIGS. 13 and 14. As in the embodiment of FIGS. 13 and 14, the physical response to the absorption of excitation radiation 18 in a material, such as human tissue (both, tissue and excitation radiation 18 not shown in FIGS. 18 and 19) is a local change in index of refraction, where the region of local change of refractive index is again designated by reference sign 20. However, the response signal is in this case an interference signal, similar to that of the embodiment of FIG. 6, rather than a deflection of a measurement beam, as was the case for the embodiment of FIGS. 13 and 14.

The apparatus of FIGS. 18 and 19 comprises a detection light beam 98, which is splitted by means of a splitter 90 in a transmitted portion 100 and a reflected portion 102. The reflected portion 102 is redirected by a mirror 104 such as to be guided in parallel to the transmitted portion 100, and both portions are located in a plane parallel to the contact surface 14 of the measurement body 16. Accordingly, unlike the embodiment of FIGS. 13 and 14, the transmitted and reflected portions 100, 102 are not reflected at the contact surface 14 of the measurement body 16.

The transmitted portion 100 of the detection light beam 98 passes a region 20 where the local change of the index of refraction occurs, while the reflected portion 102 avoids this region. Using an additional mirror 104 and a combiner 106, the two portions 100, 102 of the detection light beam 98 are recombined, and an interference signal of the recombined portions 100, 102 is recorded with an optical detector 108. Any change in the refractive index in the region 20 leads to a shift in the phase of the transmitted portion 100 and hence a change in an interference signal at the detector 108. The change in phase is bigger for bigger local changes in refractive index, such that this phase change is indicative of the degree of absorption of the excitation radiation beam 18.

Note that the embodiment of FIGS. 18 and 19 is only exemplary, and that any variant is considered herein in which two light beams are brought to interference, of which only one passes a region 20 in a measurement body 16 exposed to heat or pressure waves received from a material placed on the contact surface 14 upon absorption of excitation radiation.

Figure 20:
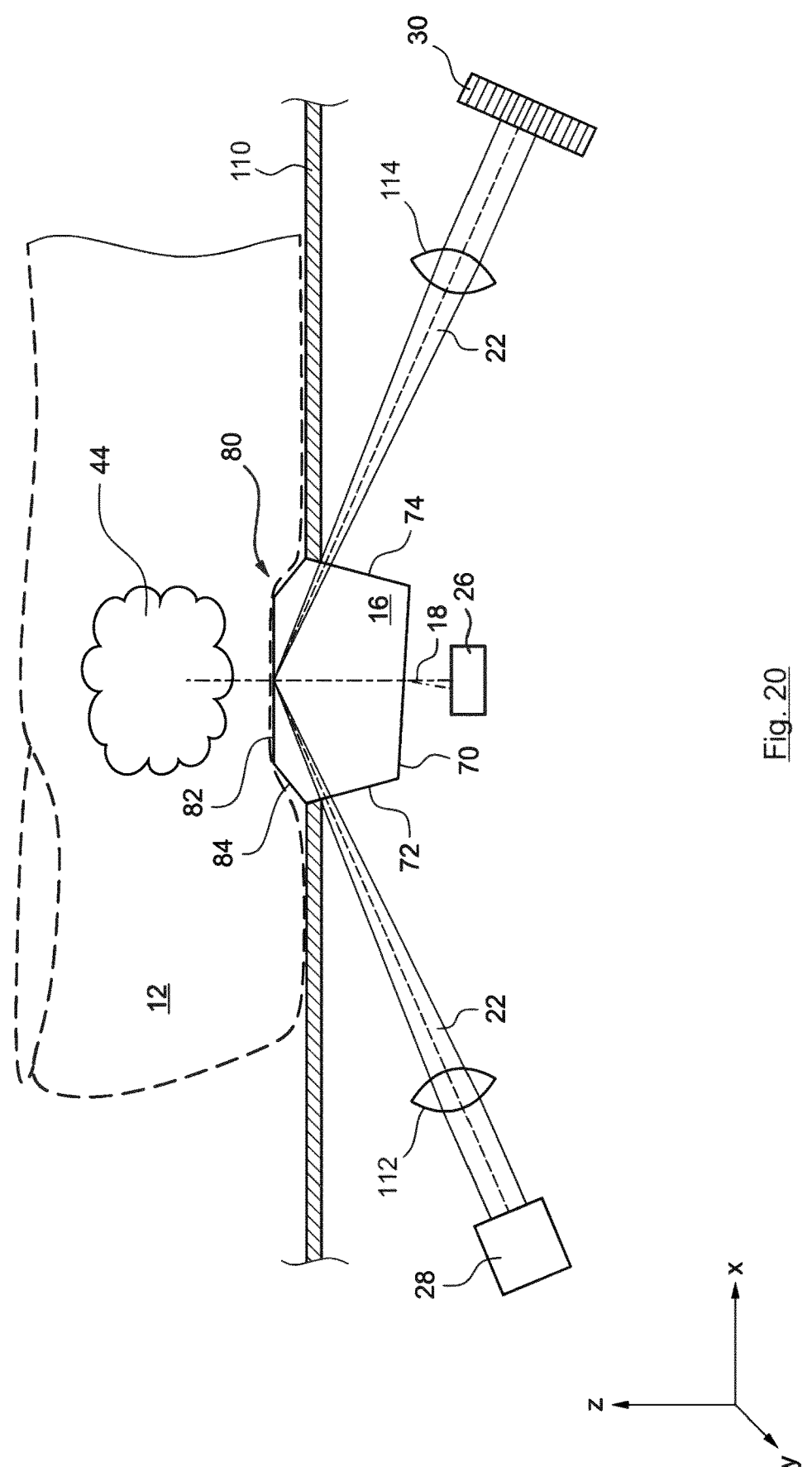
FIG. 20 is a schematic illustration of an apparatus according to one embodiment of the invention in a sectional side view in which the protrusion is formed by the measurement body.

While in the embodiment of FIG. 7, the protrusion 80 was formed on the contact surface 14 of the measurement body 16, this is not the only way to provide the protrusion. Instead, it is also possible that the measurement body itself forms the protrusion, or forms a part of the protrusion. An example of this is shown in FIG. 20, which is very similar to FIG. 7, except that the measurement body 16 is in this case much smaller and by itself forms a protrusion 80. Moreover, while in the embodiment of FIG. 7, a focusing lens 76 and a collimating lens 78 were integrated with the measurement body 16, in the embodiment of FIG. 20, these are replaced by a separate focusing lens 112 and a collimating lens 114, respectively.

As is seen in FIG. 20, the contact surface of the measurement body 16 forms the front surface 82 of the protrusion 80. Moreover, the front surface 82 of the protrusion 80 is elevated with respect to a surrounding structure, which in this case is formed by a housing wall part 110.

In the embodiment shown, the protrusion 80 formed by the measurement body 16 is of same or similar size as the protrusion 84 on the contact surface 14 in the embodiment of FIG. 7. Note that all descriptions and explanations provided above with respect to "protrusions" formed on the contact surface of a measurement body likewise apply to a protrusion formed by the measurement body 16 or formed at least in part by the measurement body 16.

Figure 21:
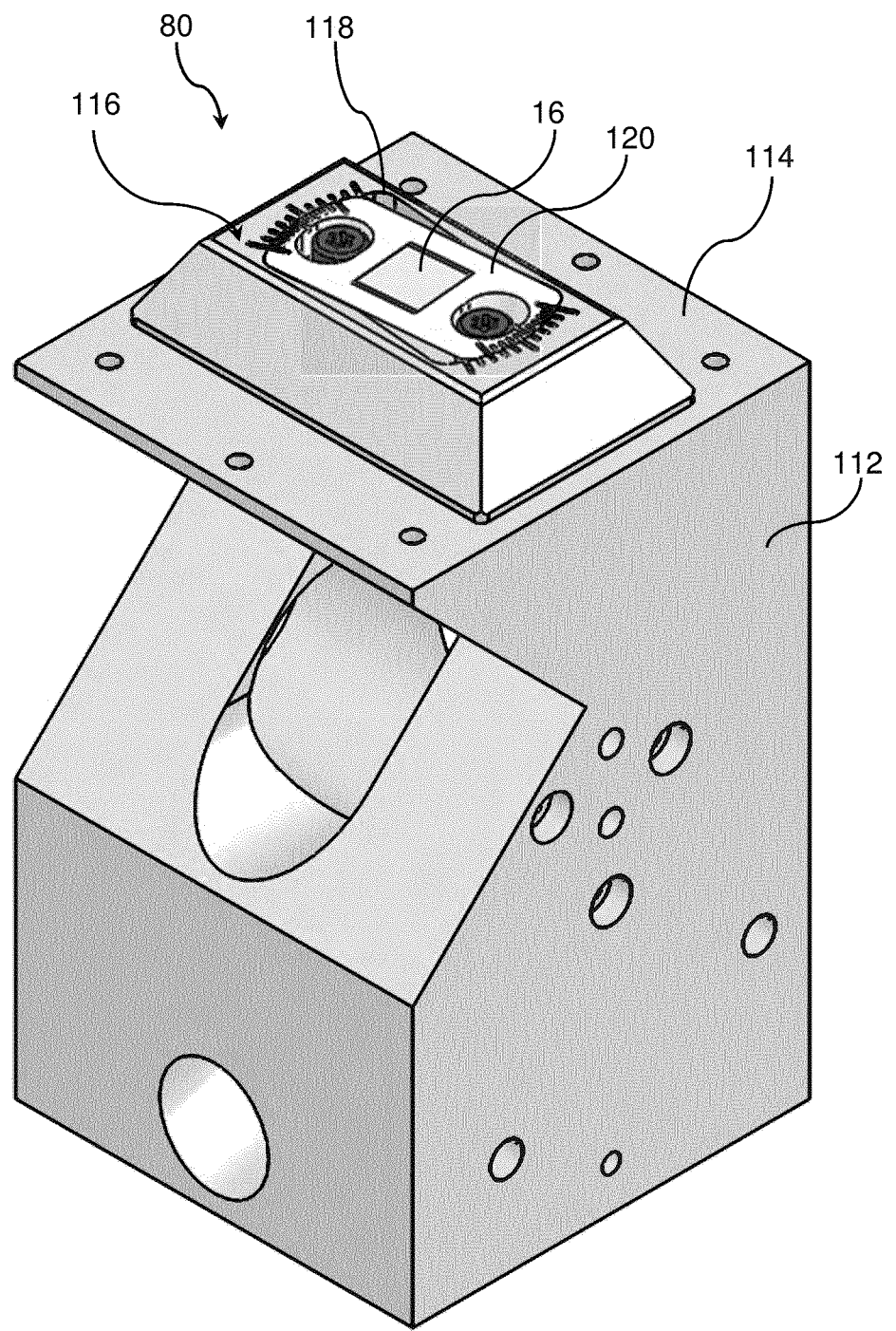
FIG. 21 is a perspective view of a support structure including a protrusion of which the measurement body is a part.
Figure 22:
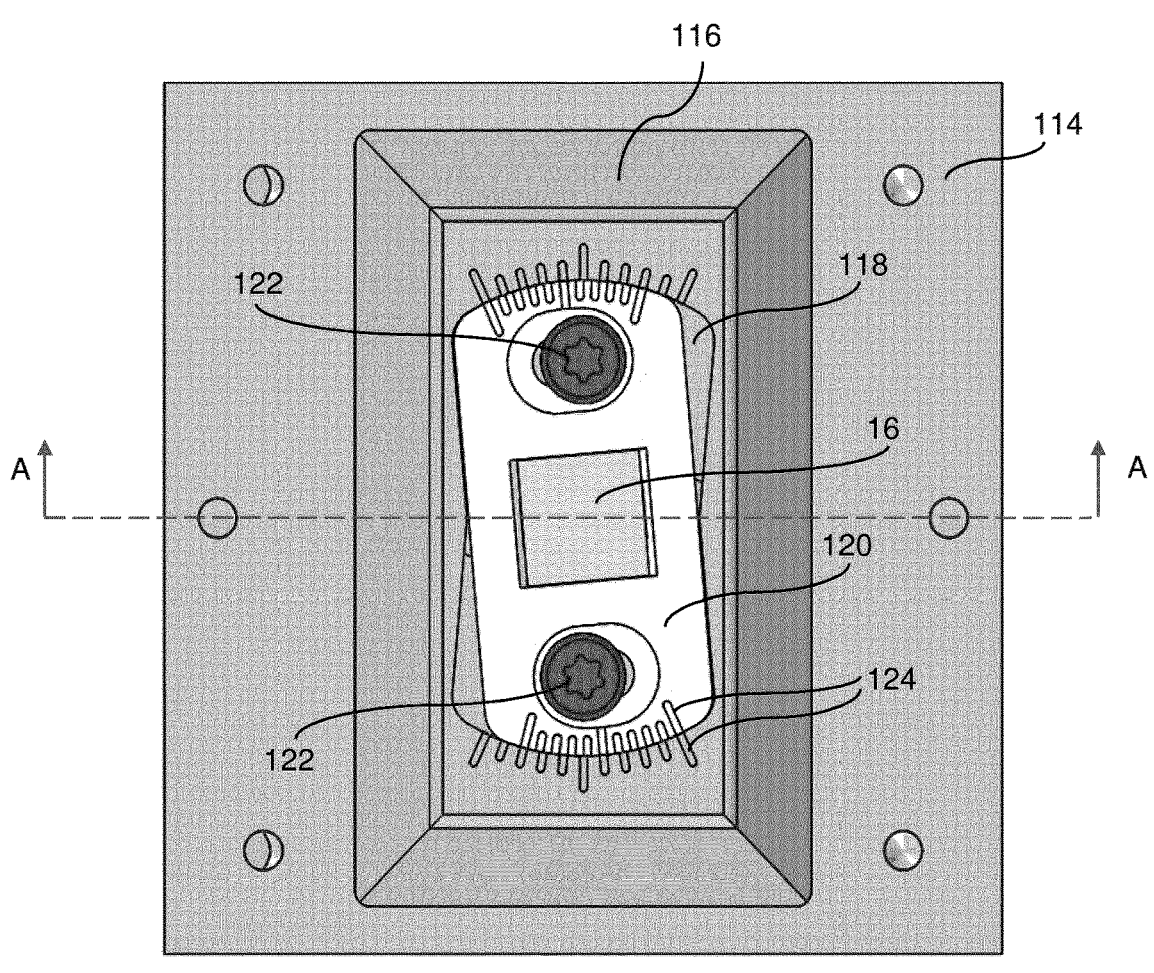
FIG. 22 is a top view of the support structure of FIG. 21.
Figure 23:
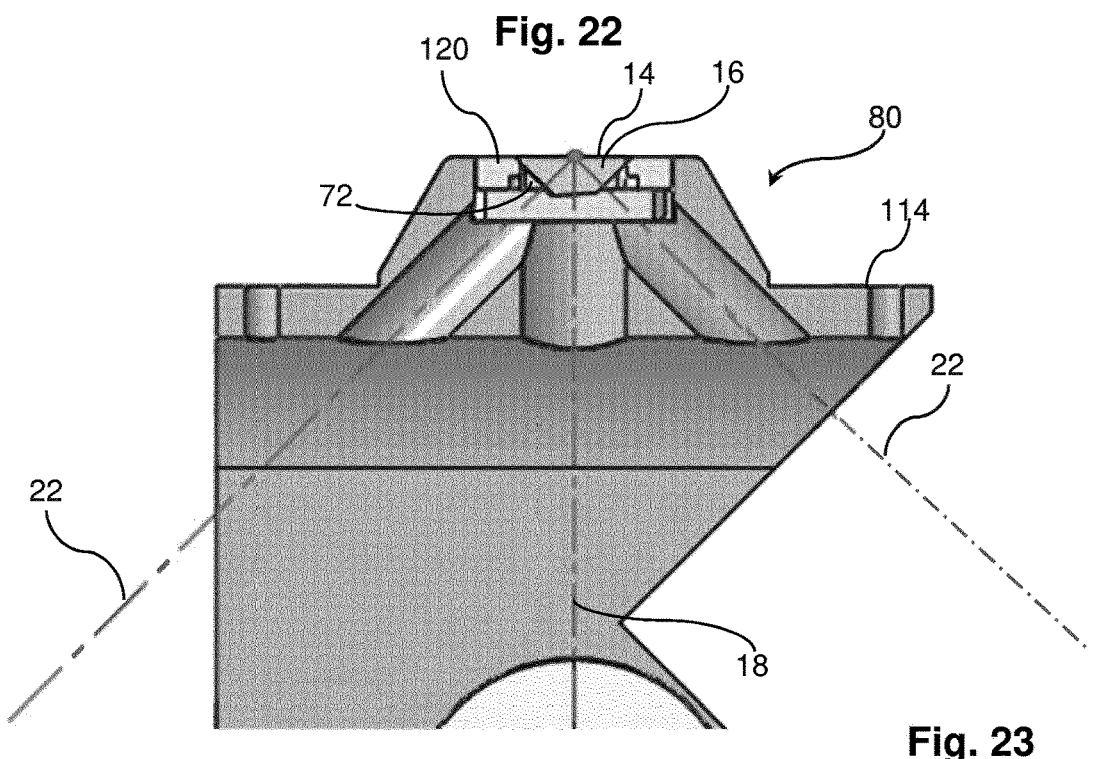
FIG. 23 is a sectional view of a part of the support structure of FIG. 21.

FIG. 21 to 23 show a further embodiment, in which the measurement body 16 forms a part of a protrusion 80. More precisely, FIG. 21 shows a mounting block 112 on which the measurement body 16 is mounted. The mounting block 112 has an upper surface 114 on which again a protrusion 80 is formed. In this case, the protrusion 80 is formed in part by a receptacle 116 in which a recess 118 is formed. The measurement body 16 is mounted in a frame 120 that is received in the recess 118 of said receptacle 116. In this case, the receptacle 116, the frame 120 and the measurement body 16 in combination form the protrusion 80, which protrudes over the top surface 114 of the mounting structure 112. Herein, the contact surface (upper surface in FIG. 21) of said measurement body 16 forms part of the front surface of the protrusion 80, which is elevated with respect to the top surface 114, which in this case forms the aforementioned "surrounding structure".

FIG. 22 shows a top view onto the protrusion 80 and the top surface 114 of the mounting structure 112. FIG. 23 shows a sectional view along the line A-A in FIG. 23. As is seen in particular from FIG. 22, the frame 120 can be turned by a few degrees around a vertical axis and can be fixed in a desired position by means of screws 122. Scales 124 are provided on both, the frame 120 and the top surface of the receptacle 116 for facilitating the adjustment of a desired rotational position.

As is seen from FIG. 23, in this embodiment, the excitation light beam 18 is directed vertically upwards. The turning axis around which the frame 120 can be turned coincides with the light beam propagation axis of the excitation light beam 18. It is seen that the excitation light beam 18 is irradiated into the material when placed on the top surface 114 and on the protrusion 80 through the contact surface 14 of the measurement body 16, wherein the contact surface 14 at the same time forms a part of the front surface of the protrusion, and in particular the part through which the excitation light beam 18 is irradiated into the material. Moreover, as is further seen in FIG. 23, this front surface is elevated with respect to the surrounding structure, i.e. either top surface 114 of the mounting structure 112.

In the embodiment shown in FIG. 21 to 23, the protrusion 80 is considerably larger than the protrusion shown in FIG. 7 or FIG. 20. In the embodiment of FIG. 21 to 23, the protrusion 80 is devised for measurement on the underside of the wrist of a person. This protrusion 80 was found to improve the contact, and in particular the coupling of the excitation light 18 into the tissue as compared to a flat surface for resting the arm thereon.

Note that in the embodiment shown in FIG. 1 to 23, the contact surface 14 of the measurement body 16 forms only a part of the top surface of the protrusion 80, but it forms the part through which the excitation radiation 18 is irradiated into the material.

By turning the frame 120 within the recess 118 of the receptacle 116, the angle of incidence of the detection light beam 22 onto the entrance surface 72 of the measurement body can be adjusted. As was explained above, the detection light beam 22 should impinge on the entrance surface at an angle of incidence with respect to the entrance surface different from 90°, such as 89° or less, 88° or less and e.g. 87.5° or less. This avoids the back reflection of the detection light beam 22 onto itself, which could lead to adverse interference effects and also possibly a damage of the detection light source. At the same time, the deviation from 90° should not be larger than necessary for this purpose. Accordingly, this angle is preferably 80° or more, more preferably 80% or more, such as 84° or 850 or more.

Further disclosed herein are the following examples:

Example 1

An apparatus for analyzing a material comprising at least one analyte, said apparatus comprising a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection device for detecting a physical response of the measurement body, or of a component included therein, to heat or a pressure wave received from said material upon absorption of said excitation radiation and for generating a response signal based on said detected physical response, said response signal being indicative of the degree of absorption of excitation radiation, wherein a pressure sensor is provided for measuring the contact pressure between the material and the measurement body.

In a preferred embodiment of Example 1, said apparatus further comprises a control system configured for receiving signals from said pressure sensor indicating the contact pressure between the material and the measurement body, wherein said control system is configured to check whether said contact pressure is below a predetermined threshold value, and in case it is found that the contact pressure is below said threshold value, to one or both of indicate lack of contact pressure to a user, prevent an analyte measurement process from starting, and interrupting a current analyte measurement process.

Example 2

An apparatus for analyzing a material comprising at least one analyte, said apparatus comprising a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection device for detecting a physical response of the measurement body, or of a component included therein, to heat or a pressure wave received from said material upon absorption of said excitation radiation and for generating a response signal based on said detected physical response, said response signal being indicative of the degree of absorption of excitation radiation, wherein said measurement body is transparent for said excitation radiation, wherein said excitation radiation source is configured for providing said excitation radiation as an excitation beam, and wherein the excitation radiation source is arranged such that said excitation beam is irradiated into said measurement body at an entrance surface, propagates through a portion of said measurement body and exits from the measurement body at said contact surface, wherein the excitation beam impinges on the entrance surface at an angle of 89.0° or less, preferably 88.0° or less, and most preferably 87.5° or less, and of 82.0° or more, preferably 84.0° or more and most preferably 85.0° or more.

In a preferred embodiment of Example 2, said excitation beam impinges on the surface of the measurement body at an angle of 90°±1.50.

In a Preferred Embodiment of Example 2, the entrance surface and the contact surface at the respective portions thereof where the excitation beam enters and leaves the measurement body, respectively are inclined with respect to each other with an angle of 1.0° or more, preferably 2.0° or more, and most preferably 2.5° or more, and 8.0° or less, preferably 6.0° or less and most preferably 5.0° or less.

Example 3

An apparatus for analyzing a material comprising at least one analyte, said apparatus comprising a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection light source for generating a detection light beam travelling through at least a portion of said measurement body or a component included in said measurement body, wherein said detection light beam is directed to be totally or partially reflected at said contact surface, wherein said detection light beam is deflected upon heat or pressure waves generated by absorption of excitation radiation in the material being transferred to said measurement body, and a detector for detecting a degree of deflection, in particular a deflection angle, of the detection light beam after its reflection at said contact surface, wherein said contact surface of the measurement body is curved in at least one principal direction in the area where the detection light beam is reflected.

In a preferred embodiment of Example 3, said curvature in said at least one principal direction corresponds to a radius of curvature in a range of 5 to 30 mm, preferably 10 to 20 mm.

In a preferred embodiment of Example 3, said curvature in said principal direction is one of concave or convex.

In a preferred embodiment of Example 3, the detection light beam prior and after reflection at said front surface forms a detection light plane, and wherein said principal direction lies within said detection light plane or forms an angle with the detection light plane that is less than 30°, preferably less than 20°.

Example 4

An apparatus for analyzing a material comprising at least one analyte, said apparatus comprising a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection light source for generating a detection light beam travelling through at least a portion of said measurement body or a component included in said measurement body, wherein said detection light beam is directed to be totally or partially reflected at said contact surface, wherein said detection light beam is deflected in response to heat or pressure waves generated by absorption of excitation radiation in the material being transferred to said measurement body, and a detector for detecting a degree of deflection, in particular a deflection angle, of the detection light beam after its reflection at said contact surface, wherein the detection light source is arranged such that said detection light beam is irradiated into said measurement body at an entrance surface, propagates through a portion of said measurement body and exits from the measurement body at an exit surface, wherein the detection beam impinges on the exit surface at an angle of 5° or more, preferably 10° or more and most preferably 150 or more with respect to the normal to the exit surface, such that the detection beam is refracted upon exiting from the accident surface of the measurement body, wherein the orientation of the exit surface with respect to the detection light beam is such that said deflection of the detection light beam in response to said heat or pressure waves being transferred to said measurement body increases said angle of said detection light beam to the normal to the exit surface.

Example 5

An apparatus for analyzing a material comprising at least one analyte, said apparatus comprising a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection light source for generating a detection light beam travelling through at least a portion of said measurement body or a component included in said measurement body, wherein said detection light beam is directed to be totally or partially reflected at said contact surface, wherein said detection light beam is deflected in response to heat or pressure waves generated by absorption of excitation radiation in the material being transferred to said measurement body, and a detector for detecting a degree of deflection, in particular a deflection angle, of the detection light beam after its reflection at said contact surface, wherein the detection light source is arranged such that said detection light beam is irradiated into said measurement body at an entrance surface, propagates through a portion of said measurement body and exits from the measurement body at an exit surface, wherein a focusing lens is attached to or formed integrally with the entrance surface for focusing said detection beam and/or a collimating lens is attached to or formed integrally with the exit surface.

Example 6

An apparatus for analyzing a material comprising at least one analyte, said apparatus comprising a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection light source for generating a detection light beam travelling through at least a portion of said measurement body or a component included in said measurement body, wherein said detection light beam is directed to be totally or partially reflected at said contact surface, wherein said detection light beam is deflected in response to heat or pressure waves generated by absorption of excitation radiation in the material being transferred to said measurement body, and a detector for detecting a degree of deflection, in particular a deflection angle, of the detection light beam after its reflection at said contact surface, wherein said detector comprises a position sensitive detector on which said detection light beam impinges, wherein said position sensitive detector is sensitive for detecting shifts in position of the detection light beam impinging thereon in at least one sensing direction, wherein said position sensitive detector is arranged such that said deflection of said detection light beam leads to a shift of the position of the detection light beam impinging thereon in said at least one sensing direction, and wherein a cylinder lens is provided in the light path of the detection light beam for shaping the profile of the detection light beam and/or the position sensitive detector is arranged at an angle deviating from 90° from the detection light beam, such that the diameter of the detection light beam impinging on said position sensitive detector in said sensing direction is at least 1.5 times as large, preferably at least 2.0 times as large as the diameter of the detection light beam in a direction orthogonal to said sensing direction.

In a preferred embodiment of Example 6, the cylinder lens is a collimating lens arranged in said light path of the detection light beam between its reflection at said contact surface and said position sensitive detector, wherein said cylinder lens is arranged to collimate said detection light beam predominantly in a dimension orthogonal to said sensing direction of said position sensitive detector, wherein said cylindrical collimating lens is preferably formed integrally with an exit surface of said measurement body at which the detection light beam exits from the measurement body.

Example 7

An apparatus for analyzing a material comprising at least one analyte, said apparatus comprising a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection light source for generating a detection light beam travelling through at least a portion of said measurement body or a component included in said measurement body, wherein said detection light beam is directed to be totally or partially reflected at said contact surface, wherein said detection light beam is deflected in response to heat or pressure waves generated by absorption of excitation radiation in the material being transferred to said measurement body, and a detector for detecting a degree of deflection, in particular a deflection angle, of the detection light beam after its reflection at said contact surface, further comprising a beam splitter for splitting a source light beam into said detection light beam and a reference light beam, wherein said reference light beam is likewise directed to be totally or partially reflected at a surface of said measurement body that is in thermal or pressure-transmitting contact with said material, but in a region where any effect of heat or pressure waves received from the material upon absorption of excitation radiation is negligible, and wherein said detection device comprises an additional detection device for detecting a degree of deflection, in particular a deflection angle, of the reference light beam after its reflection at said contact surface, wherein said additional detection device preferably comprises a photodetector, in particular a position sensitive photodetector Example 8

An apparatus for analyzing a material comprising at least one analyte, said apparatus comprising a measurement body having a contact surface suitable to be brought in thermal contact or pressure-transmitting contact with said material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection device for detecting a physical response of the measurement body, or of a component included therein, to heat or a pressure wave received from said material upon absorption of said excitation radiation and for generating a response signal based on said detected physical response, said response signal being indicative of the degree of absorption of excitation radiation, wherein said apparatus comprises a fiber embedded in said measurement body, a detection light source provided at one end of said fiber for coupling detection light into said fiber and a mode detector provided at the other end of said fiber, said mode detector being suitable for detecting changes in optical modes of said detection light in response to the heat or pressure waves received by the measurement body from said material, wherein said changes in optical modes preferably comprise a shift or a rotation of optical modes within the fiber.

While the present invention has been described in terms of specific embodiments, it is understood that variations and modifications will occur to those in the art, all of which are intended as aspects of the present invention. Accordingly, only such limitations as appear in the claims should be placed on the invention.

The invention claimed is:

1. An apparatus for analyzing a material comprising at least one analyte, said apparatus comprising:

a measurement body having a contact surface suitable to be brought in thermal contact or pressure-transmitting contact with the material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection device for detecting a physical response of said measurement body, or of a component included therein, to heat or a pressure wave received from the material upon absorption of said excitation radiation and for generating a response signal based on said detected physical response, said response signal being indicative of the degree of absorption of excitation radiation, wherein said measurement body is transparent for said excitation radiation, wherein said excitation radiation source is configured for providing said excitation radiation as an excitation beam, wherein said excitation radiation source is arranged such that said excitation beam is irradiated into said measurement body at an entrance surface thereof, propagates through a portion of said measurement body and exits from said measurement body at the contact surface, wherein said excitation beam impinges on the entrance surface at an angle of 89.0° or less and of 82.0° or more, and wherein the entrance surface and the contact surface at the respective portions thereof where said excitation beam enters and leaves said measurement body, respectively, are inclined with respect to each other with an angle of 1.0° or more and 8.0° or less.

2. The apparatus of claim 1, wherein said excitation beam impinges on the contact surface of said measurement body at an angle of 90°±1.5°.

3. The apparatus of claim 1, wherein said detection device comprises a light source for generating a detection light beam travelling through at least a portion of said measurement body or a component included in said measurement body, said physical response of said measurement body to heat or pressure waves received from the material upon absorption of said excitation radiation is a local change in the refractive index of said measurement body or said component, and said detection device is configured for detecting one of a change in the light path or a change in the phase of detection beam due to said change in refractive index.

4. The apparatus of claim 3, wherein said detection device is configured such that the detection light beam is irradiated into said measurement body at the entrance surface, wherein the detection light beam impinges on the entrance surface at an angle of incidence with respect to the entrance surface of 89° or less and of 80° or more.

5. The apparatus of claim 4, wherein said measurement body is received in a frame or receptacle that is configured to turn said measurement body to adjust said angle of incidence of the detection light beam when impinging on the entrance surface of said measurement body, wherein said frame or receptacle is configured to turning said measurement body around an axis parallel with the excitation light beam, or deviating from parallel by less than 10°.

6. The apparatus of claim 3, wherein said measurement body is transparent for the detection light beam, the detection light beam is directed to be totally or partially reflected at a surface of said measurement body that is in thermal or pressure-transmitting contact with the material, and wherein said detection device comprises a detector for detecting a degree of deflection of the detection light beam after its reflection at the contact surface, due to said local change in refractive index.

7. The apparatus of claim 6, wherein the detection light source is arranged such that the detection light beam is irradiated into said measurement body at the entrance surface, propagates through a portion of said measurement body and exits from said measurement body at an exit surface, wherein a focusing lens is formed integrally with the entrance surface for focusing the detection light beam entering into said measurement body in at least one dimension or a collimating lens is formed integrally with the exit surface for collimating the detection light beam in at least one dimension, or both.

8. The apparatus of claim 7, wherein at least one of said focusing lens and said collimating lens is a cylinder lens focusing and collimating the detection light beam at least predominantly in one dimension, respectively.

9. The apparatus of claim 1, wherein said detection device comprises an interferometric device configured to assess said change in phase of the detection beam and generate a response signal indicative of said change in phase.

10. The apparatus of claim 1, wherein said measurement body or a component in said measurement body has electrical properties that change in response to a local change in temperature or a change in pressure associated therewith, and wherein said detection device comprises electrodes for capturing electrical signals representing said electrical properties.

11. The apparatus of claim 1, wherein said apparatus comprises an optical fiber embedded in said measurement body, a detection light source provided at one end of said fiber for coupling detection light into said optical fiber and a mode detector provided at the other end of said fiber, said mode detector being suitable for detecting changes in optical modes of said detection light in response to the heat or pressure waves received by said measurement body from the material.

12. The apparatus of claim 1, wherein the material is human skin and said analyte is glucose present in the skin.

13. The apparatus of claim 1, wherein said excitation radiation is generated using an array of quantum cascade lasers, each having a dedicated wavelength.

14. The apparatus of claim 1, wherein said excitation radiation is generated using at least one tunable quantum cascade laser.

15. The apparatus of claim 1, wherein some or all of said excitation radiation has wavelengths in a range of 5 μm to 13 μm.

16. An apparatus for analyzing a material comprising at least one analyte, said apparatus comprising:

a measurement body having a contact surface suitable to be brought in thermal contact or pressure-transmitting contact with the material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection device for detecting a physical response of said measurement body, or of a component included therein, to heat or a pressure wave received from the material upon absorption of said excitation radiation and for generating a response signal based on said detected physical response, said response signal being indicative of the degree of absorption of excitation radiation, wherein said measurement body is transparent for said excitation radiation, wherein said excitation radiation source is configured for providing said excitation radiation as an excitation beam, wherein said excitation radiation source is arranged such that said excitation beam is irradiated into said measurement body at an entrance surface thereof, propagates through a portion of said measurement body and exits from said measurement body at the contact surface, wherein said excitation beam impinges on the entrance surface at an angle of 89.0° or less and of 82.0° or more, wherein said detection device comprises a light source for generating a detection light beam travelling through at least a portion of said measurement body or a component included in said measurement body, said physical response of said measurement body to heat or pressure waves received from the material upon absorption of said excitation radiation is a local change in the refractive index of said measurement body or said component, and said detection device is configured for detecting one of a change in the light path or a change in the phase of detection beam due to said change in refractive index, wherein said measurement body is transparent for the detection light beam, the detection light beam is directed to be totally or partially reflected at a surface of said measurement body that is in thermal or pressure-transmitting contact with the material, wherein said detection device comprises a detector for detecting a degree of deflection of the detection light beam after its reflection at the contact surface, due to said local change in refractive index, wherein the detection light source is arranged such that the detection light beam is irradiated into said measurement body at the entrance surface, propagates through a portion of said measurement body and exits from said measurement body at an exit surface, wherein the detection light beam impinges—in absence of any deflection due to said local change in refractive index—on the exit surface at an angle of 5° or more with respect to the normal to the exit surface, such that the detection beam is refracted upon exiting from the exit surface of said measurement body, and wherein the orientation of the exit surface with respect to the detection light beam is such that said deflection of the detection light beam in response to said heat or pressure waves being transferred to said measurement body increases said angle between the detection light beam and the normal to the exit surface.

17. An apparatus for analyzing a material comprising at least one analyte, said apparatus comprising:

a measurement body having a contact surface suitable to be brought in thermal contact or pressure-transmitting contact with the material, said thermal or pressure-transmitting contact permitting heat or pressure waves generated by absorption of excitation radiation in the material to be transferred to said measurement body, an excitation radiation source configured for irradiating excitation radiation into the material to be absorbed therein, and a detection device for detecting a physical response of said measurement body, or of a component included therein, to heat or a pressure wave received from the material upon absorption of said excitation radiation and for generating a response signal based on said detected physical response, said response signal being indicative of the degree of absorption of excitation radiation, wherein said measurement body is transparent for said excitation radiation, wherein said excitation radiation source is configured for providing said excitation radiation as an excitation beam, wherein said excitation radiation source is arranged such that said excitation beam is irradiated into said measurement body at an entrance surface thereof, propagates through a portion of said measurement body and exits from said measurement body at the contact surface, wherein said excitation beam impinges on the entrance surface at an angle of 89.0° or less and of 82.0° or more, wherein said detection device comprises a light source for generating a detection light beam travelling through at least a portion of said measurement body or a component included in said measurement body, said physical response of said measurement body to heat or pressure waves received from the material upon absorption of said excitation radiation is a local change in the refractive index of said measurement body or said component, and said detection device is configured for detecting one of a change in the light path or a change in the phase of detection beam due to said change in refractive index, wherein said measurement body is transparent for the detection light beam, the detection light beam is directed to be totally or partially reflected at a surface of said measurement body that is in thermal or pressure-transmitting contact with the material, wherein said detection device comprises a detector for detecting a degree of deflection of the detection light beam after its reflection at the contact surface, due to said local change in refractive index, wherein said detector comprises a position sensitive detector on which the detection light beam impinges, wherein said position sensitive detector is sensitive for detecting shifts in position of the detection light beam impinging thereon in at least one sensing direction, wherein said position sensitive detector is arranged such that said deflection of the detection light beam leads to a shift of the position of the detection light beam impinging thereon in said at least one sensing direction, and wherein a cylinder lens is provided in the light path of the detection light beam for shaping the profile of the detection light beam or the position sensitive detector is arranged at an angle with respect to the detection light beam deviating from 90°, such that the diameter of the detection light beam impinging on said position sensitive detector in said sensing direction is at least 1.5 times as large as the diameter of the detection light beam in a direction orthogonal to said sensing direction.

18. The apparatus of claim 17, wherein said cylinder lens is a collimating lens arranged in said light path of the detection light beam between its reflection at the contact surface and said position sensitive detector, wherein said cylinder lens is arranged to collimate the detection light beam at least predominantly in a dimension orthogonal to said sensing direction of said position sensitive detector.

19. An apparatus for analyzing a material comprising at least one analyte, said apparatus comprising:

a measurement body having a contact surface suitable to be brought in thermal contact or pressure-transmitting contact with the material, said thermal or pressure-transmitting contact permitting heat or pressure waves generated by absorption of excitation radiation in the material to be transferred to said measurement body, an excitation radiation source configured for irradiating excitation radiation into the material to be absorbed therein, a detection device for detecting a physical response of said measurement body, or of a component included therein, to heat or a pressure wave received from the material upon absorption of said excitation radiation and for generating a response signal based on said detected physical response, said response signal being indicative of the degree of absorption of excitation radiation, wherein said measurement body is transparent for said excitation radiation, and a beam splitter for splitting a source light beam into a detection light beam and a reference light beam, wherein said excitation radiation source is configured for providing said excitation radiation as an excitation beam, wherein said excitation radiation source is arranged such that said excitation beam is irradiated into said measurement body at an entrance surface thereof, propagates through a portion of said measurement body and exits from said measurement body at the contact surface, wherein said excitation beam impinges on the entrance surface at an angle of 89.0° or less and of 82.0° or more, wherein said detection device comprises a light source for generating the detection light beam travelling through at least a portion of said measurement body or a component included in said measurement body, said physical response of said measurement body to heat or pressure waves received from the material upon absorption of said excitation radiation is a local change in the refractive index of said measurement body or said component, and said detection device is configured for detecting one of a change in the light path or a change in the phase of detection beam due to said change in refractive index, wherein said measurement body is transparent for the detection light beam, the detection light beam is directed to be totally or partially reflected at a surface of said measurement body that is in thermal or pressure-transmitting contact with the material, wherein said detection device comprises a detector for detecting a degree of deflection of the detection light beam after its reflection at the contact surface, due to said local change in refractive index, wherein said reference light beam is directed to be totally or partially reflected at a surface of said measurement body that is in thermal or pressure-transmitting contact with the material, but in a region where any effect of heat or pressure waves received from the material upon absorption of excitation radiation is negligible, and wherein said detection device comprises an additional detection device for detecting a degree of deflection of the reference light beam after its reflection at the contact surface.

20. A method of analyzing a material comprising at least one analyte, said method comprising:

bringing a measurement body having a contact surface in thermal contact or pressure-transmitting contact with the material, said thermal or pressure-transmitting contact permitting heat or pressure waves generated by absorption of excitation radiation in the material to be transferred to said measurement body, irradiating excitation radiation into the material to be absorbed therein, and detecting a physical response of said measurement body, or of a component included therein, to heat or a pressure wave received from the material upon absorption of said excitation radiation and generating a response signal based on said detected physical response, said response signal being indicative of the degree of absorption of excitation radiation, wherein said measurement body is transparent for said excitation radiation, wherein an excitation radiation source provides said excitation radiation as an excitation beam, wherein said excitation beam is irradiated into said measurement body at an entrance surface thereof, propagates through a portion of said measurement body and exits from said measurement body at the contact surface, wherein said excitation beam impinges on the entrance surface at an angle of 89.0° or less and of 82.0° or more, and wherein the entrance surface and the contact surface at the respective portions thereof where said excitation beam enters and leaves said measurement body, respectively, are inclined with respect to each other with an angle of 1.0° or more and 8.0° or less.

21. The method of claim 20, wherein said excitation beam impinges on the contact surface of said measurement body at an angle of 90°±1.5°.

22. The method of claim 20, wherein said detection comprises generating a detection light beam travelling through at least a portion of said measurement body or a component included in said measurement body, said physical response of said measurement body to heat or pressure waves received from the material upon absorption of said excitation radiation is a local change in the refractive index of said measurement body or said component, and wherein said detecting comprises detecting one of a change in the light path or a change in the phase of detection beam due to said change in refractive index.

23. The method of claim 22, wherein the detection light beam is irradiated into said measurement body at the entrance surface such that the detection light beam impinges on the entrance surface at an angle of incidence with respect to the entrance surface of 89° or less and of 80° or more.

24. The apparatus of claim 23, wherein said measurement body is received in a frame or receptacle that is configured to turn said measurement body to adjust said angle of incidence of the detection light beam when impinging on the entrance surface of said measurement body, said frame or receptacle is configured to turning said measurement body around an axis parallel with the excitation light beam, or deviating from parallel by less than 10°.

25. The method of claim 22, wherein said measurement body is transparent for the detection light beam, the detection light beam is directed to be totally or partially reflected at a surface of said measurement body that is in thermal or pressure-transmitting contact with the material, and wherein said detection comprises detecting a degree of deflection of the detection light beam after its reflection at the contact surface, due to said local change in refractive index.

26. The method of claim 20, wherein the detection light beam is irradiated into said measurement body at the entrance surface, propagates through a portion of said measurement body and exits from said measurement body at an exit surface, wherein a focusing lens is formed integrally with the entrance surface for focusing the detection light beam entering into said measurement body in at least one dimension or a collimating lens is formed integrally with the exit surface for collimating the detection light beam in at least one dimension.

27. The method of claim 20, wherein said detection comprises using an interferometric device configured to assessing said change in phase of the detection beam and generate a response signal indicative of said change in phase.

28. The method of claim 20, wherein said measurement body or a component in said measurement body has electrical properties that change in response to a local change in temperature or a change in pressure associated therewith, and wherein said detection device comprises electrodes for capturing electrical signals representing said electrical properties.

29. The method of claim 20, wherein an optical fiber is embedded in said measurement body, a detection light source is provided at one end of said fiber for coupling detection light into said optical fiber and a mode detector is provided at the other end of said fiber, wherein using said mode detector, changes in optical modes of said detection light in response to the heat or pressure waves received by said measurement body from the material are detected.

30. The method of claim 20, wherein the material is human skin, and said analyte is glucose present in the interstitial fluid of the skin.

31. The method of claim 20, further comprising a step of generating said excitation radiation using an array of quantum cascade lasers, each having a dedicated wavelength.

32. The method of one of claim 20, further comprising a step of generating said excitation radiation using at least one tunable quantum cascade laser.

33. The method of claim 20, wherein some or all of said excitation radiation has wavelengths in a range of 5 μm to 13 μm.

34. A method of analyzing a material comprising at least one analyte, said method comprising:

bringing a measurement body having a contact surface in thermal contact or pressure-transmitting contact with the material, said thermal or pressure-transmitting contact permitting heat or pressure waves generated by absorption of excitation radiation in the material to be transferred to said measurement body, irradiating excitation radiation into the material to be absorbed therein, and detecting a physical response of said measurement body, or of a component included therein, to heat or a pressure wave received from the material upon absorption of said excitation radiation and generating a response signal based on said detected physical response, said response signal being indicative of the degree of absorption of excitation radiation, wherein said measurement body is transparent for said excitation radiation, wherein an excitation radiation source provides said excitation radiation as an excitation beam, wherein said excitation beam is irradiated into said measurement body at an entrance surface thereof, propagates through a portion of said measurement body and exits from said measurement body at the contact surface, wherein said excitation beam impinges on the entrance surface at an angle of 89.0° or less and of 82.0° or more, wherein said detection comprises generating a detection light beam travelling through at least a portion of said measurement body or a component included in said measurement body, said physical response of said measurement body to heat or pressure waves received from the material upon absorption of said excitation radiation is a local change in the refractive index of said measurement body or said component, wherein said detecting comprises detecting one of a change in the light path or a change in the phase of detection beam due to said change in refractive index, wherein said measurement body is transparent for the detection light beam, the detection light beam is directed to be totally or partially reflected at a surface of said measurement body that is in thermal or pressure-transmitting contact with the material, and wherein said detection comprises detecting a degree of deflection of the detection light beam after its reflection at the contact surface, due to said local change in refractive index, wherein the detection light source is arranged such that the detection light beam is irradiated into said measurement body at the entrance surface, propagates through a portion of said measurement body and exits from said measurement body at an exit surface, wherein the detection light beam impinges—in absence of any deflection due to said local change in refractive index—on the exit surface at an angle of 5° or more with respect to the normal to the exit surface, such that the detection beam is refracted upon exiting from the exit surface of said measurement body, and wherein the orientation of the exit surface with respect to the detection light beam is such that said deflection of the detection light beam in response to said heat or pressure waves being transferred to said measurement body increases said angle between the detection light beam and the normal to the exit surface.

35. The method of claim 26, wherein at least one of said focusing lens and said collimating lens is a cylinder lens focusing and collimating the detection light beam at least predominantly in one dimension, respectively.

36. A method of analyzing a material comprising at least one analyte, said method comprising:

bringing a measurement body having a contact surface in thermal contact or pressure-transmitting contact with the material, said thermal or pressure-transmitting contact permitting heat or pressure waves generated by absorption of excitation radiation in the material to be transferred to said measurement body, irradiating excitation radiation into the material to be absorbed therein, and detecting a physical response of said measurement body, or of a component included therein, to heat or a pressure wave received from the material upon absorption of said excitation radiation and generating a response signal based on said detected physical response, said response signal being indicative of the degree of absorption of excitation radiation, wherein said measurement body is transparent for said excitation radiation, wherein an excitation radiation source provides said excitation radiation as an excitation beam, wherein said excitation beam is irradiated into said measurement body at an entrance surface thereof, propagates through a portion of said measurement body and exits from said measurement body at the contact surface, wherein said excitation beam impinges on the entrance surface at an angle of 89.0° or less and of 82.0° or more, wherein said detection comprises generating a detection light beam travelling through at least a portion of said measurement body or a component included in said measurement body, said physical response of said measurement body to heat or pressure waves received from the material upon absorption of said excitation radiation is a local change in the refractive index of said measurement body or said component, wherein said detecting comprises detecting one of a change in the light path or a change in the phase of detection beam due to said change in refractive index, wherein said measurement body is transparent for the detection light beam, the detection light beam is directed to be totally or partially reflected at a surface of said measurement body that is in thermal or pressure-transmitting contact with the material, wherein said detection comprises detecting a degree of deflection of the detection light beam after its reflection at the contact surface, due to said local change in refractive index, wherein said detector comprises a position sensitive detector on which the detection light beam impinges, wherein said position sensitive detector detects shifts in position of the detection light beam impinging thereon in at least one sensing direction, wherein said position sensitive detector is arranged such that said deflection of the detection light beam leads to a shift of the position of the detection light beam impinging thereon in said at least one sensing direction, and wherein a cylinder lens is provided in the light path of the detection light beam for shaping the profile of the detection light beam or the position sensitive detector is arranged at an angle deviating from 90° from the detection light beam, such that the diameter of the detection light beam impinging on said position sensitive detector in said sensing direction is at least 1.5 times as large as the diameter of the detection light beam in a direction orthogonal to said sensing direction.

37. The method of claim 36, wherein said cylinder lens is a collimating lens arranged in said light path of the detection light beam between its reflection at the contact surface and said position sensitive detector, wherein said cylinder lens collimates the detection light beam at least predominantly in a dimension orthogonal to said sensing direction of said position sensitive detector.

38. A method of analyzing a material comprising at least one analyte, said method comprising:

bringing a measurement body having a contact surface in thermal contact or pressure-transmitting contact with the material, said thermal or pressure-transmitting contact permitting heat or pressure waves generated by absorption of excitation radiation in the material to be transferred to said measurement body, irradiating excitation radiation into the material to be absorbed therein, and detecting a physical response of said measurement body, or of a component included therein, to heat or a pressure wave received from the material upon absorption of said excitation radiation and generating a response signal based on said detected physical response, said response signal being indicative of the degree of absorption of excitation radiation, wherein said measurement body is transparent for said excitation radiation, wherein an excitation radiation source provides said excitation radiation as an excitation beam, wherein said excitation beam is irradiated into said measurement body at an entrance surface thereof, propagates through a portion of said measurement body and exits from said measurement body at the contact surface, wherein said excitation beam impinges on the entrance surface at an angle of 89.0° or less and of 82.0° or more, wherein said detection comprises generating a detection light beam travelling through at least a portion of said measurement body or a component included in said measurement body, said physical response of said measurement body to heat or pressure waves received from the material upon absorption of said excitation radiation is a local change in the refractive index of said measurement body or said component, wherein said detecting comprises detecting one of a change in the light path or a change in the phase of detection beam due to said change in refractive index, wherein said measurement body is transparent for the detection light beam, the detection light beam is directed to be totally or partially reflected at a surface of said measurement body that is in thermal or pressure-transmitting contact with the material, and wherein said detection comprises detecting a degree of deflection of the detection light beam after its reflection at the contact surface, due to said local change in refractive index, and wherein a source light beam is splitted into the detection light beam and a reference light beam, wherein said reference light beam is likewise directed to be totally or partially reflected at a surface of said measurement body that is in thermal or pressure-transmitting contact with the material, but in a region where any effect of heat or pressure waves received from the material upon absorption of excitation radiation is negligible, and wherein a degree of deflection, in particular a deflection angle, of the reference light beam after its reflection at the contact surface is detected.

* * * * *